US007148371B2

(12) United States Patent
Nakazawa et al.

(10) Patent No.: US 7,148,371 B2
(45) Date of Patent: Dec. 12, 2006

(54) METHOD FOR PRODUCING LYSINE DERIVATIVE

(75) Inventors: Masakazu Nakazawa, Kawasaki (JP);
Daisuke Takahashi, Kawasaki (JP);
Masaki Naito, Kawasaki (JP);
Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/211,442

(22) Filed: Aug. 26, 2005

(65) Prior Publication Data

US 2006/0004103 A1  Jan. 5, 2006

Related U.S. Application Data

(60) Division of application No. 10/639,513, filed on Aug. 13, 2003, now Pat. No. 7,012,152, which is a division of application No. 10/281,977, filed on Oct. 29, 2002, now Pat. No. 6,664,412, which is a continuation of application No. 09/903,531, filed on Jul. 13, 2001, now abandoned.

(30) Foreign Application Priority Data

Jul. 13, 2000 (JP) .............................. 2000-213181
Nov. 1, 2000 (JP) .............................. 2000-334579
Apr. 17, 2001 (JP) .............................. 2001-118508

(51) Int. Cl.
*C07C 229/00* (2006.01)
(52) U.S. Cl. ................................. 560/169
(58) Field of Classification Search ............. None
See application file for complete search history.

(56) References Cited

U.S. PATENT DOCUMENTS 3,534,074 A  10/1970  Feuer et al. ............. 260/404.5
6,504,047 B1  1/2003  Knaup ........................ 560/169

FOREIGN PATENT DOCUMENTS

| EP | 0 515 698 | 12/1992 |
|----|-----------|---------|
| JP | 54-8749   | 4/1979  |
| JP | 56-3034   | 1/1981  |
| JP | 63-24895  | 2/1988  |
| JP | 64-71476  | 3/1989  |
| JP | 3-19696   | 1/1991  |

OTHER PUBLICATIONS

S. Nagarjan, et al., J. Org. Chem., vol. 51, No. 25, pp. 4856-4861, "Chemistry of Naturally Occurring Polyamines. 10.[1] Nonmetabolizable Derivatives of Spermine and Spermidine", 1986.
J.A. Robl, et al., Journal of Medicinal Chemistry, vol. 42, No. 2, pp. 305-311, "Vasopeptidase Inhibitors: Incorporation of Geminal and Spirocyclic Substituted Azepinones in Mercaptoacyl Dipeptides", 1999.

*Primary Examiner*—Zachary C. Tucker
(74) *Attorney, Agent, or Firm*—Oblon, Spivak, McClelland, Maier & Neustadt, P.C.

(57) ABSTRACT

The present invention provides a method for industrially producing an optically active lysine derivative useful as a pharmaceutical intermediate. More particularly, the present invention provides a production method including protecting an amino group or an amino group and carboxyl group of optically active 2-amino-6-methyl-6-nitroheptanoic acid with a protecting group, reducing a nitro group to synthesize a 6,6-dimethyl lysine derivative and reacting the 6,6-dimethyl lysine derivative with an acetic acid derivative.

2 Claims, No Drawings

METHOD FOR PRODUCING LYSINE DERIVATIVE

CROSS-REFERENCE TO RELATED APPLICATIONS

The present application is a divisional of U.S. Ser. No. 10/639,513, filed on Aug. 13, 2003, now U.S. Pat. No 7,012,152 which is a divisional of U.S. Ser. No. 10/281,977, filed on Oct. 29, 2002, now U.S. Pat. No 6,664,412, which is a continuation of U.S. Ser. No. 09/903,531, filed on Jul. 13, 2001, now abandoned which claims priority to Japanese application No. JP 2001-118508, filed on Apr. 17, 2001, Japanese application No. JP 2000-334579, filed on Nov. 1, 2000, and Japanese application No. JP 2000-213181, filed on Jul. 13, 2000.

TECHNICAL FIELD OF THE INVENTION

The present invention relates to a method for producing a specific, optically active lysine derivative useful as a pharmaceutical intermediate.

BACKGROUND OF THE INVENTION

Optically active lysine derivatives, such as an optically active 6,6-dimethyl lysine derivative of the formula (3)

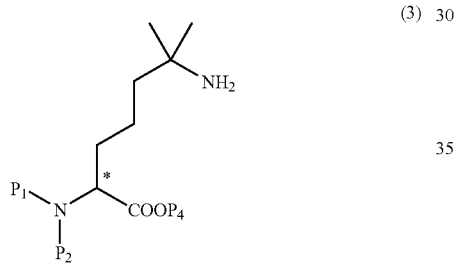

(3)

wherein * means an asymmetric carbon atom, $P_1$ and $P_2$ are each independently an amino-protecting group or hydrogen atom where $P_1$ and $P_2$ are not hydrogen atoms at the same time, or $P_1$ and $P_2$ in combination show an amino-protecting group, and $P_4$ is a hydrogen atom or carboxyl-protecting group, and an optically active lysine derivative of the formula (5)

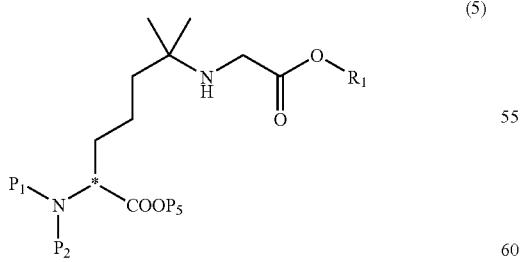

(5)

wherein *, $P_1$ and $P_2$ are as defined above, $R_1$ is alkyl group having 1 to 6 carbon atoms or aralkyl group having 7 to 12 carbon atoms, and $P_5$ is a hydrogen atom or carboxyl-protecting group, are useful as pharmaceutical intermediates.

For example, a compound having an S-configuration of asymmetric carbon atom is an important intermediate compound for a pharmaceutical compound of the following formula (25), which is useful as an antihypertensive agent having an inhibitory activity against an angiotensin converting enzyme (ACE) and neutral endopeptidase (NEP) (*Journal of Medicinal Chemistry*, 1999, 42, 305–311).

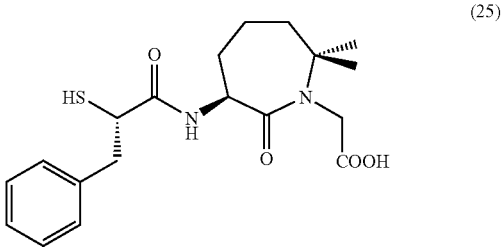

(25)

As a method for producing the pharmaceutical compound of the formula (25), *Journal of Medicinal Chemistry*, 1999, 42, 305–311 discloses a method shown by the following scheme using (S)-2-phthalimido-6-hydroxyhexanoic acid as a starting material.

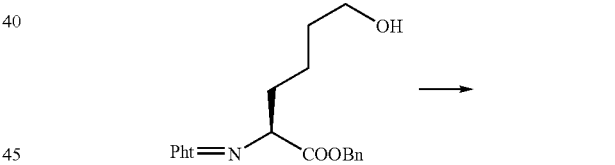

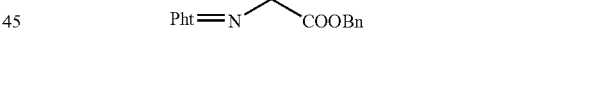

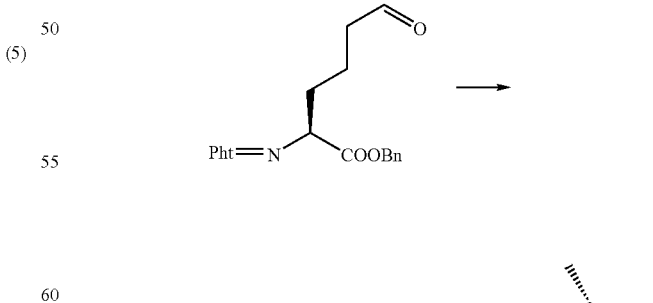

-continued

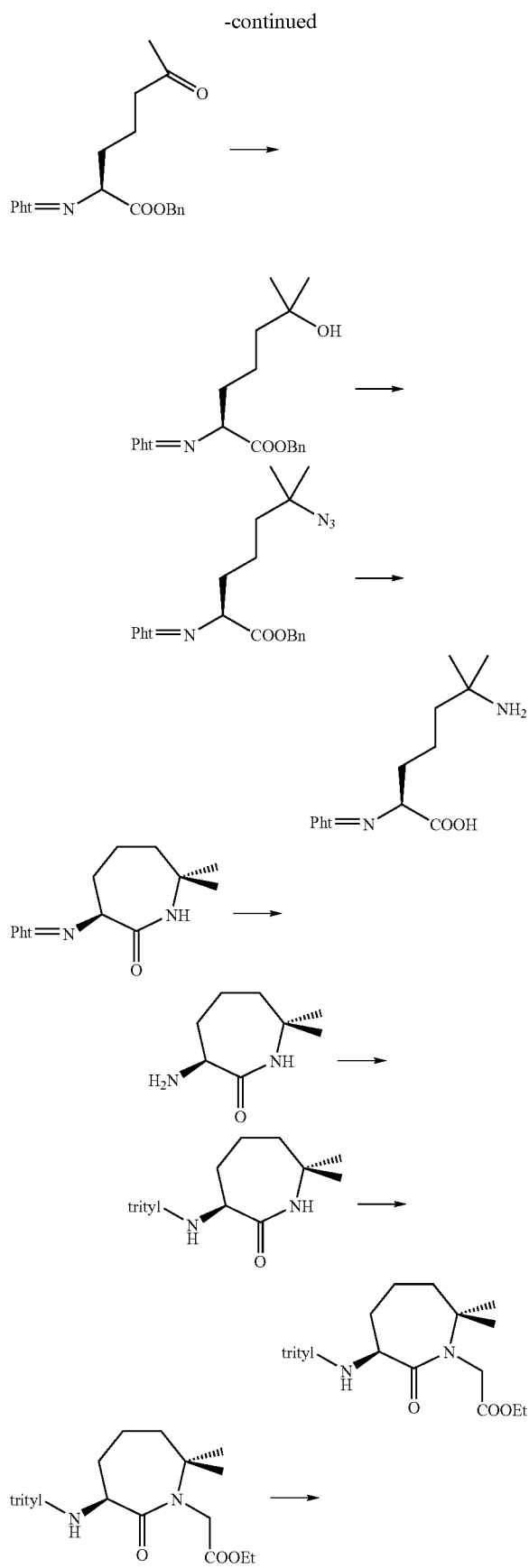

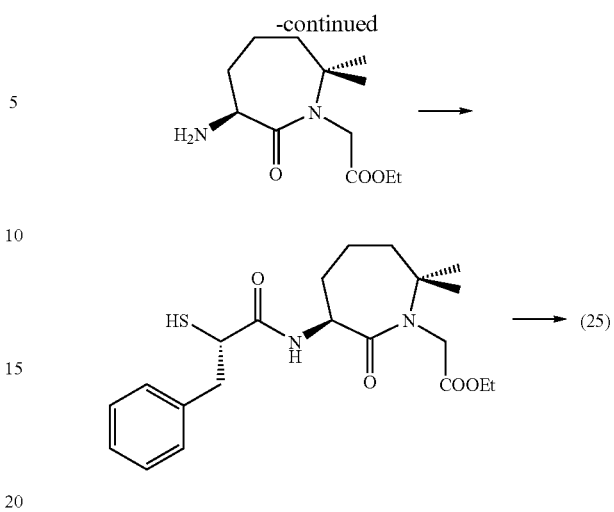

However, this method requires-many steps, and there is a demand on a production method that permits easier and simpler industrial production.

It is also known that an optically active amino acid can be generated by directly applying a microorganism enzyme system to 5-substituted hydantoin as a starting material. When a microorganism enzyme system is used, an enzyme (hydantoinase) to hydrolyze a 5-substituted hydantoin compound and produce N-carbamyl-amino acid, and an enzyme (N-carbamyl-amino-acid hydrolase) to enantio-selectively decompose the produced N-carbamyl-amino acid into optically active amino acid are required.

Conventionally, there are methods for producing D-amino acid using microorganisms containing these two kinds of enzymes, or substances containing such enzymes, such as a method comprising the use of bacteria of the genus *Pseudomonas* (JP-B-56-003034), a method comprising the use of bacteria of the genus *Agrobacterium* (JP-A-03-019696) and the like.

As a method for producing L-amino acid, there are known a method comprising the use of bacteria of the genus *Flavobacterium* (JP-B-56-008749), a method comprising the use of bacteria of the genus *Bacillus* (JP-A-63-24895), a method comprising the use of bacteria of the genus *Pseudomonas* (JP-A-01-071476), a method comprising the use of bacteria of the genus *Arthrobacter* [*J. Biotechnol.*, Vol. 46, p. 63 (1996)] and the like.

It has been also reported that optically active amino acid can be produced by isolating a genetic DNA of hydantoinase and a genetic DNA of N-carbamyl-amino-acid hydrolase from various bacteria and expressing them in *E. coli* [*Biotechnol. Prog.*, vol. 16, p. 564 (2000), EP515698 and the like].

It has been detailed that the substrate specificity of these hydantoinase and N-carbamyl-amino-acid hydrolase is rather broad, and by a combined use of these two kinds of enzymes under the limitation of the substrate specificity, natural or nonnatural various amino acids having optical activity can be produced from 5-substituted hydantoin compound [*Enzyme Catalysis in Organic Synthesis*, K. Drauz et al. ed., vol. 1, ch. B2.4, pp. 409–431, VCH (1995)]. Because the producible optically active amino acid is limited due to its substrate specificity, however, an optically active amino acid corresponding to 5-substituted hydantoin compound is not always generated. For example, *Microbacterium liquefaciens* AJ3940 strain (formerly classified under *Flavobacterium* sp.) that affords L-tryptophan in a high yield from 5-indolylmethylhydantoin (racemate) acts well on 5-substituted hydantoin having an aromatic ring, and can generate many kinds of L-enantiomer of aromatic amino acids such as L-phenylalanine, L-tyrosine and the like. However, since it does not act at all on 5-methylhydantoin, 5-sec-butylhydantoin, 5-carboxymethylhydantoin or 5-carboxyethylhydantoin, and does not produce the corresponding L-alanine, L-isoleucine, L-aspartic acid or L-glutamic acid, it is known to be specific to compounds having an aromatic ring [*Agric. Biol. Chem.*, vol. 51, p. 729 (1987)].

SUMMARY OF THE INVENTION

It is therefore an object of the present invention to provide an industrial method for producing optically active lysine derivatives represented by the aforementioned formulas (3) and (5), which are useful as pharmaceutical intermediates.

The present inventors have conducted intensive studies in an attempt to solve the aforementioned problems and found a completely novel reaction sequence industrially superior as a method for producing compounds of the aforementioned formulas (3) and (5). To be specific, it has been found that the aforementioned object can be achieved by the process including protecting an amino group and, where necessary, a carboxyl group of optically active 2-amino-6-methyl-6-nitroheptanoic acid with a protecting group, after which nitro group is reduced to synthesize a 6,6-dimethyl lysine derivative of the formula (3), and further by reacting the 6,6-dimethyl lysine derivative with an acetic acid derivative to synthesize an optically active lysine derivative of the formula (5).

More particularly, the present invention provides the following.

[1] A method for producing an optically active lysine derivative of the formula (5)

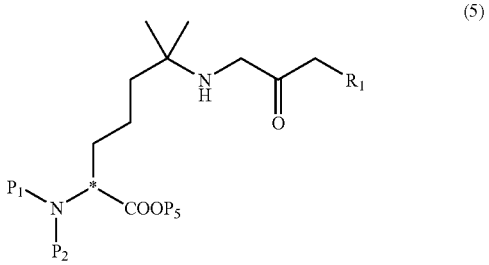

wherein
* means an asymmetric carbon atom,
$P_1$ and $P_2$ are each independently an amino-protecting group or hydrogen atom where $P_1$ and $P_2$ are not hydrogen atoms at the same time, or $P_1$ and $P_2$ in combination show an amino-protecting group,
$R_1$ is alkyl group having 1 to 6 carbon atoms or aralkyl group having 7 to 12 carbon atoms, and
$P_5$ is a hydrogen atom or carboxyl-protecting group or a salt thereof, which method comprises the steps of (1) protecting an amino group or an amino group and a carboxyl group of optically active 2-amino-6-methyl-6-nitroheptanoic acid of the formula (1)

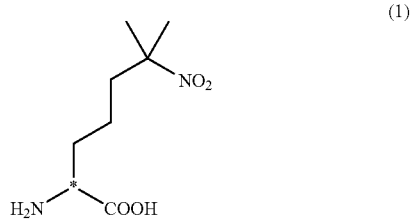

wherein * is as defined above, or a salt thereof, with a protecting group to give an optically active amino acid derivative of the formula (2)

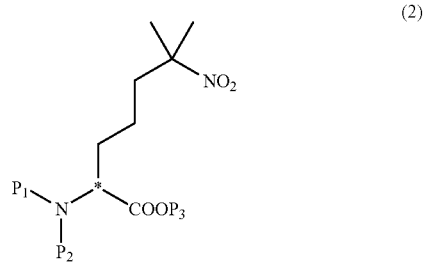

wherein *, $P_1$ and $P_2$ are as defined above and $P_3$ is a hydrogen atom or carboxyl-protecting group, (2) reducing a nitro group of the derivative of the formula (2) to give an optically active 6,6-dimethyl lysine derivative of the formula (3)

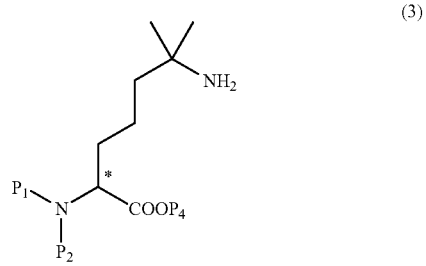

wherein *, $P_1$ and $P_2$ are as defined above and $P_4$ is a hydrogen atom or carboxyl-protecting group, or a salt thereof, and (3) reacting the derivative of the formula (3) or a salt thereof with an acetate derivative of the formula (4)

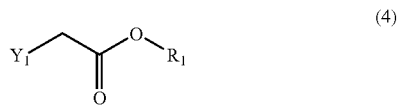

wherein $Y_1$ is a leaving group and $R_1$ is as defined above.

[2] The method of [1], wherein the reduction is a catalytic reduction using a transition metal catalyst and metallic sulfate.

[3] The method of [1], wherein the reduction is a catalytic reduction using a palladium catalyst and ferrous sulfate.

[4] The method of [1]), wherein either $P_1$ or $P_2$ is a tert-butoxycarbonyl group and the other is a hydrogen atom, $P_3$, $P_4$ and $P_5$ are methyl groups and $R_1$ is a tert-butyl group.

[5] A method for producing an optically active 6,6-dimethyl lysine derivative of the aforementioned formula (3) or a salt thereof, which method comprises protecting an amino group or an amino group and a carboxyl group of optically active 2-amino-6-methyl-6-nitroheptanoic acid of the above-mentioned formula (1) or a salt thereof with a protecting group to give an optically active amino acid derivative of the above-mentioned formula (2), and reducing a nitro group of the derivative of the formula (2).

[6] The method of [5], wherein the reduction is a catalytic reduction using a transition metal catalyst and metallic sulfate.

[7] The method of [5], wherein the reduction is a catalytic reduction using a palladium catalyst and ferrous sulfate.

[8] The method of [5], wherein either $P_1$ or $P_2$ is a tert-butoxycarbonyl group and the other is a hydrogen atom and $P_3$ and $P_4$ are methyl groups.

[9] A method for producing an optically active 6,6-dimethyl lysine derivative of the aforementioned formula (3) or a salt thereof, which method comprises reducing an amino acid derivative of the above-mentioned formula (2).

[10] The method of [9], wherein the reduction is a catalytic reduction using a transition metal catalyst and metallic sulfate.

[11] The method of [9], wherein the reduction is a catalytic reduction using a palladium catalyst and ferrous sulfate.

[12] The method of [9], wherein either $P_1$ or $P_2$ is a tert-butoxycarbonyl group and the other is a hydrogen atom and $P_3$ and $P_4$ are methyl groups.

[13] A method for producing an optically active lysine derivative of the aforementioned formula (5) or a salt thereof, which method comprises reacting an optically active 6,6-dimethyl lysine derivative of the above-mentioned formula (3) or a salt thereof with an acetate derivative of the above-mentioned formula (4).

[14] The method of [13], wherein either $P_1$ or $P_2$ is a tert-butoxycarbonyl group and the other is a hydrogen atom, $P_4$ and $P_5$ are methyl groups and $R_1$ is a tert-butyl group.

[15] The method of [1], wherein the optically active 2-amino-6-methyl-6-nitroheptanoic acid of the above-mentioned formula (1) is produced by the following steps (a)–(c):

(a) reacting a 4-methyl-4-nitropentane derivative of the formula (6)

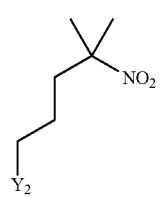

wherein $Y_2$ is a leaving group, with 2-acylaminomalonic diester of the formula (7)

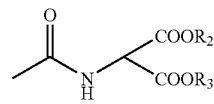

wherein $R_2$ and $R_3$ are each independently alkyl group having 1 to 6 carbon atoms or aralkyl group having 7 to 12 carbon atoms, to give 2-acylamino-2-(4-methyl-4-nitropentyl)malonic diester of the formula (8)

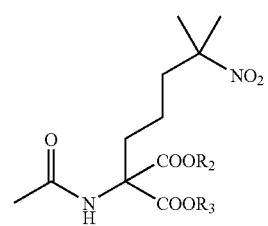

wherein $R_2$ and $R_3$ are as defined above;

(b) subjecting 2-acylamino-2-(4-methyl-4-nitropentyl)malonic diester of the formula (8) to hydrolysis and decarboxylation to give 2-acetylamino-6-methyl-6-nitroheptanoic acid (racemate) of the formula (9)

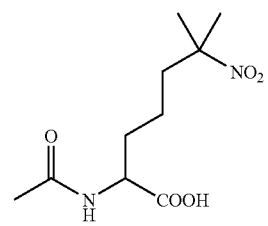

and (c) having acylase act on 2-acetylamino-6-methyl-6-nitroheptanoic acid (racemate) of the formula (9) to give optically active 2-amino-6-methyl-6-nitroheptanoic acid of the formula (1) or a salt thereof.

[16] The method of [1], wherein the optically active 2-amino-6-methyl-6-nitroheptanoic acid of the above-mentioned formula (1) is produced by the following steps (d)–(g):

(d) reducing 5-(4-methyl-4-nitropentylidene)hydantoin of the formula (10)

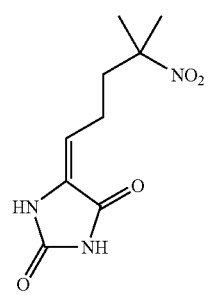

to give 5-(4-methyl-4-nitropentyl)hydantoin of the formula (11)

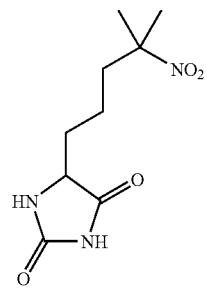
(11)

(e) hydrolyzing 5-(4-methyl-4-nitropentyl)hydantoin of the formula (11) to give 2-amino-6-methyl-6-nitroheptanoic acid (racemate) of the formula (12)

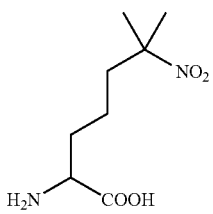
(12)

(f) acylating an amino group of 2-amino-6-methyl-6-nitroheptanoic acid of the formula (12) to give 2-acylamino-6-methyl-6-nitroheptanoic acid (racemate) of the formula (13)

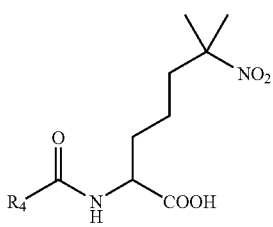
(13)

wherein $R_4$ is methyl group or phenyl group; and (g) having acylase act on 2-acylamino-6-methyl-6-nitroheptanoic acid (racemate) of the formula (13) to give optically active 2-amino-6-methyl-6-nitroheptanoic acid of the formula (1) or a salt thereof.

[17] A compound of any of the formulas (14)–(18), a salt thereof, an optically active substance thereof or a racemate thereof:

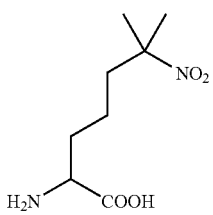
(14)

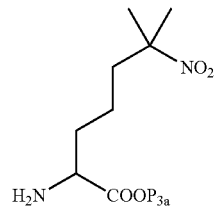
(15)

(16)

(17)

(18)

wherein $P_1$ and $P_2$ are each independently an amino-protecting group or hydrogen atom where $P_1$ and $P_2$ are not hydrogen atoms at the same time, or $P_1$ and $P_2$ in combination show an amino-protecting group except phthaloyl group, $P_{3a}$ is a carboxyl-protecting group and $P_4$ is a hydrogen atom or a carboxyl-protecting group.

[18] A compound of any of the formulas (19)–(23):

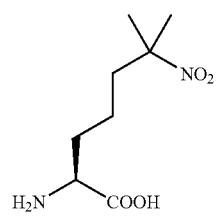
(19)

-continued

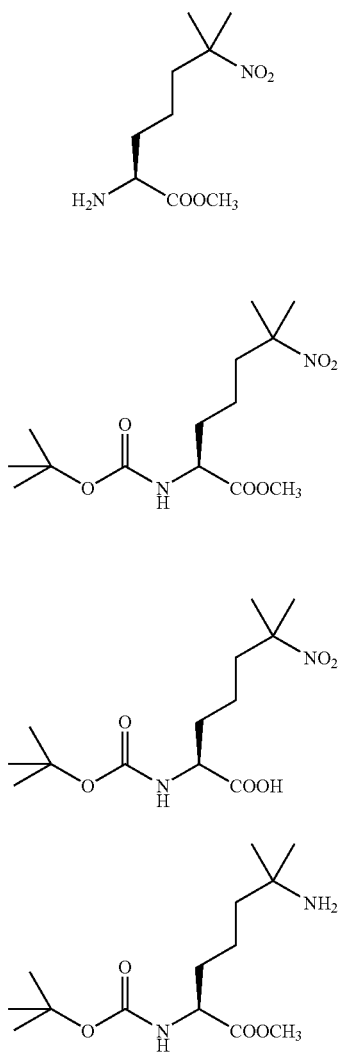

or a salt thereof.

[19] A compound of any of the formulas (6), (8), (10), (11) and (24) or a salt thereof:

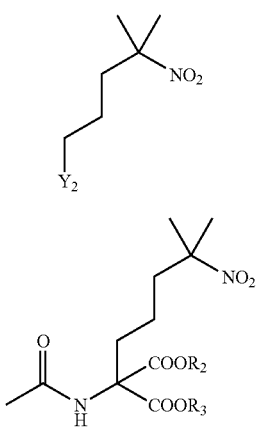

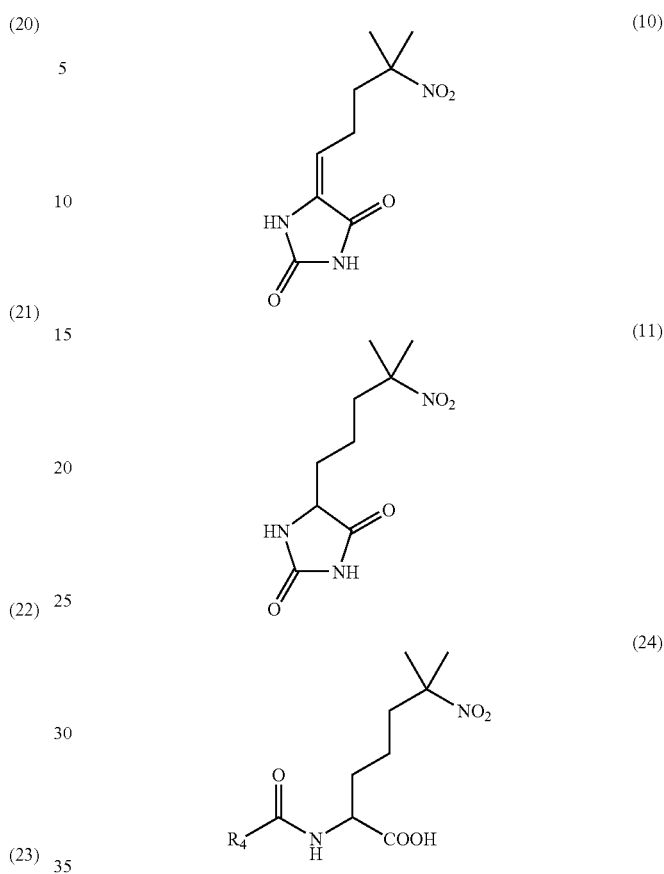

wherein $Y_2$ is a leaving group except chlorine atom, $R_4$ is methyl group or phenyl group, and $R_2$ and $R_3$ are each independently alkyl group having 1 to 6 carbon atoms or aralkyl group having 7 to 12 carbon atoms, and wherein the compounds of the formulas (8) and (24) comprise their optically active substances and racemates.

[20] The method of [1], wherein the optically active 2-amino-6-methyl-6-nitroheptanoic acid of the above-mentioned formula (1) is produced via the following step (h):

(h) enantio-selectively hydrolyzing 5-(4-methyl-4-nitropentyl)hydantoin of the formula (11)

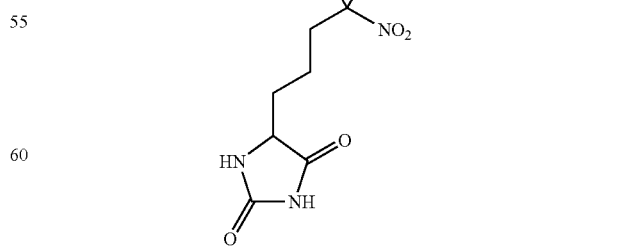

using at least one member selected from the group consisting of a microorganism, a treated product of a microorganism, hydantoinase and N-carbamyl-amino-acid hydrolase to give optically active 2-amino-6-methyl-6-nitroheptanoic acid of the formula (1) or a salt thereof.

[21] The method of [20], wherein said microorganism, and the origin of said treated product of a microorganism, said hydantoinase and said N-carbamyl-amino-acid hydrolase are bacteria of the genus *Agrobacterium*, the genus *Bacillus* or the genus *Microbacterium*.

[22] The method of [20], wherein said microorganism, and the origin of said treated product of a microorganism, said hydantoinase and said N-carbamyl-amino-acid hydrolase are bacteria of the genus *Agrobacterium*, and the optically active 2-amino-6-methyl-6-nitroheptanoic acid or a salt thereof is D-2-amino-6-methyl-6-nitroheptanoic acid or a salt thereof.

[23] The method of [20], wherein said microorganism, and the origin of said treated product of a microorganism, said hydantoinase and said N-carbamyl-amino-acid hydrolase are bacteria of the genus *Bacillus* or the genus *Microbacterium*, and said optically active 2-amino-6-methyl-6-nitroh-eptanoic acid or a salt thereof is L-2-amino-6-methyl-6-nitroheptanoic acid or a salt thereof.

DETAILED DESCRIPTION OF THE INVENTION

In the formulas of the present invention, $P_1$ and $P_2$ are each independently an amino-protecting group or hydrogen atom, where $P_1$ and $P_2$ are not hydrogen atoms at the same time (that is, when the amino group does not have a protecting group). Alternatively, $P_1$ and $P_2$ in combination form an amino-protecting group. The amino-protecting group is not particularly limited, and may be, for example, the protecting group and the like disclosed in *Protecting Groups in Organic Chemistry* 2nd edition (John Wiley & Sons, Inc. 1991). A typical protecting group is exemplified by benzyloxycarbonyl group (Z group), 9-fluorenyl-methoxycarbonyl group (Fmoc group), tert-butoxycarbonyl group (Boc group), methoxycarbonyl group (Moc group) and the like. The protecting group when $P_1$ and $P_2$ in combination form an amino-protecting group is exemplified by phthaloyl group and the like.

According to the present invention, one of $P_1$ and $P_2$ is particularly preferably tert-butoxycarbonyl group, and the other is hydrogen atom.

In the formulas of the present invention, $P_3$, $P_4$ and $P_5$ are each hydrogen atom or carboxyl-protecting group. The carboxyl-protecting group is not particularly limited, and may be, for example, alkyl group having 1 to 6 carbon atoms, aryl group having 6 to 10 carbon atoms and the like. Specific examples thereof include methyl group, ethyl group, n-propyl group, isopropyl group, n-butyl group, isobutyl group, sec-butyl group, t-butyl group, phenyl group and the like. The carboxyl-protecting group shown by $P_3$, $P_4$ and $P_5$ in the present invention is particularly preferably methyl group.

In the formulas of the present invention, $P_{3a}$ is a carboxyl-protecting group which is the same as the aforementioned carboxyl-protecting group at $P_3$.

In the formulas of the present invention, $R_1$ is alkyl group having 1 to 6 carbon atoms or aralkyl group having 7 to 12 carbon atoms. Examples of the alkyl group having 1 to 6 carbon atoms include methyl group, ethyl group, n-propyl group, isopropyl group, n-butyl group, isobutyl group, sec-butyl group, t-butyl group and the like. Examples of the aralkyl group having 7 to 12 carbon atoms include benzyl group and the like. As $R_1$, tert-butyl group is particularly preferable.

In the formulas of the present invention, $R_2$ and $R_3$ are each independently alkyl group having 1 to 6 carbon atoms or aralkyl group having 7 to 12 carbon atoms. Examples of alkyl group having 1 to 6 carbon atoms include methyl group, ethyl group, n-propyl group, isopropyl group, n-butyl group, isobutyl group, sec-butyl group, t-butyl group and the like. Examples of aralkyl group having 7 to 12 carbon atoms include benzyl group and the like. As $R_2$ and $R_3$, alkyl group having 1 to 6 carbon atoms is preferable, alkyl group having 1 to 4 carbon atoms is more preferable, and ethyl group is particularly preferable. $R_2$ and $R_3$ are preferably the same.

In the present invention, $Y_1$ in the formula (4) and $Y_2$ in the formula (6) are each a leaving group. The leaving group means an atom or atomic group that is released from a reaction substrate by a substitution reaction, elimination reaction and the like, and is exemplified by chlorine, bromine, iodine, p-toluenesulfonyloxy group, mesyloxy group, trifluoromethanesulfonyloxy group, alkylcarbonate group, phenylcarbonate group, or saturated or unsaturated acyloxy group having 1 to 8 carbon atoms and the like.

A preferable leaving group is bromine atom or iodine atom.

A typical compound preferably produced by the production method of the present invention is a compound of the formula (3), such as Nα-t-butoxycarbonyl-6,6-dimethyl-L-lysine methyl ester of the following formula (23), and a compound of the formula (5), such as Nα-t-butoxycarbonyl-Nε-t-butoxycarbonylmethyl-6,6-dimethyl-L-lysine methyl ester of the formula (26).

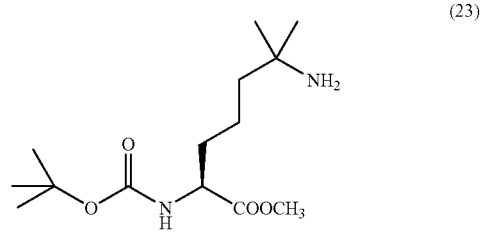

(23)

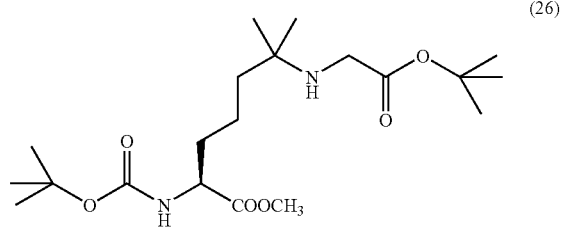

(26)

A method for producing the amino acid derivative of the aforementioned formula (1), which is the starting material in the present invention, is explained in the following.

The amino acid derivative of the formula (1) can be synthesized by three routes (I), (II) and (III) as shown in the following reaction scheme.

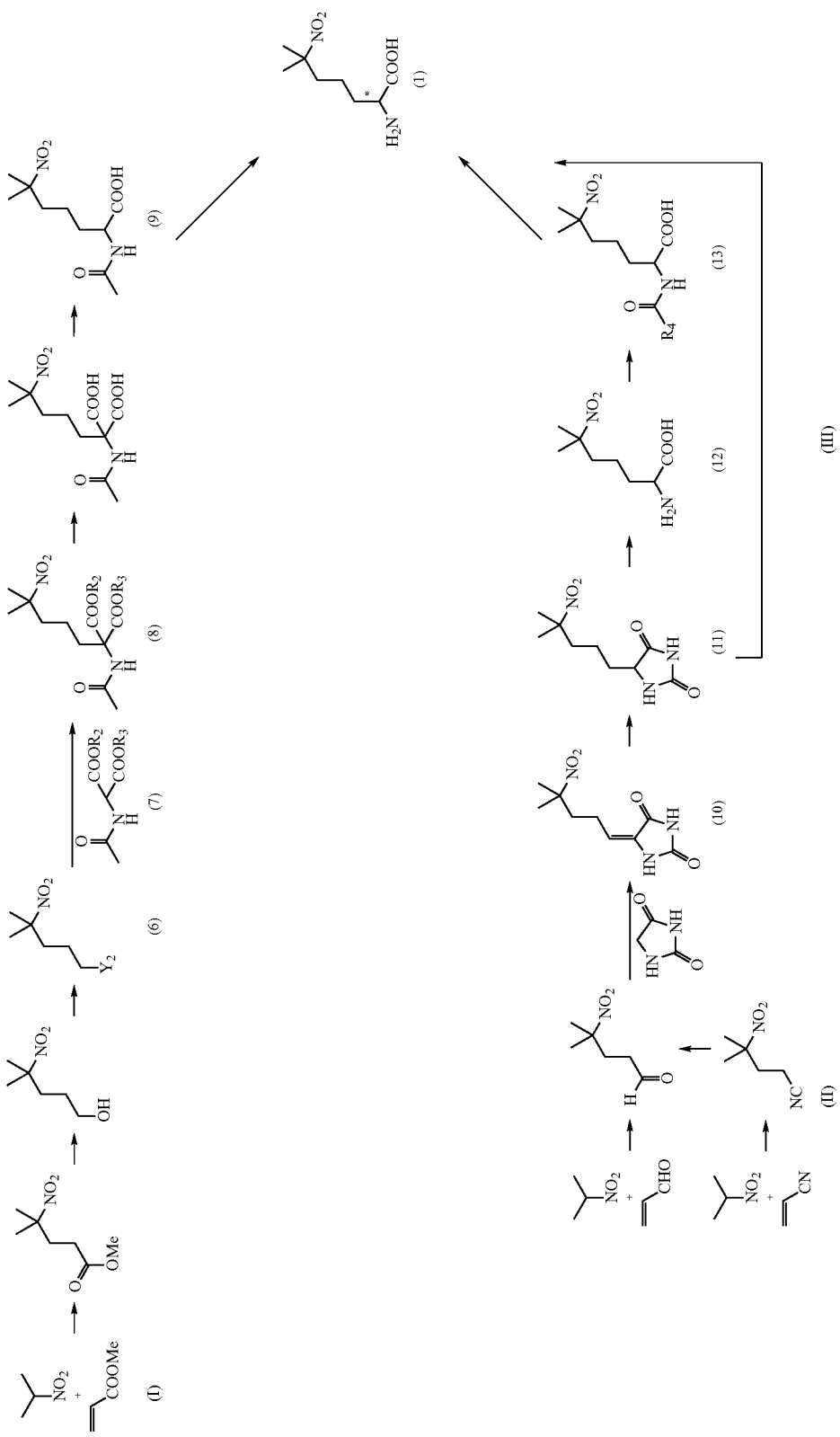

wherein *, $R_2$, $R_3$, $R_4$ and $Y_2$ are as defined above.

The route (I) is explained in the following.

(i) A catalytic amount of potassium fluoride is added to 2-nitropropane and methyl acrylate, and the mixture is refluxed under heating in a suitable solvent such as ethanol and the like. The reaction mixture is concentrated (or evaporated) and extracted to give methyl 4-methyl-4-nitropentanoate (Bulletin of the Chemical Society of Japan 1966, 39 (11), 2549–2551). The obtained methyl 4-methyl-4-nitropentanoate can be isolated and/or purified by a conventional method, such as distillation, chromatography and the like, but generally, can be used in the next step without isolation and/or purification.

(ii) Methyl 4-methyl-4-nitropentanoate obtained above is reacted with at least 2 equivalents of a reducing agent, such as sodium borohydride and the like, in a suitable solvent, such as ethanol and the like, by stirring the mixture at room temperature—a refluxing temperature, preferably 40° C.–70° C., for about 1–24 h, preferably about 2–5 h. The reaction mixture is concentrated (or evaporated) and extracted to give 4-methyl-4-nitropentanol. The obtained 4-methyl-4-nitropentanol can be isolated and/or purified by a conventional method, such as distillation, chromatography and the like, but generally, can be used in the next step without isolation and/or purification.

(iii) By substituting the hydroxyl group of 4-methyl-4-nitropentanol for a leaving group, a 4-methyl-4-nitropentane derivative of the aforementioned formula (6) is obtained by a method known to those of ordinary skill in the art. For example, substitution for a preferable leaving group, such as halogen atom (e.g., bromine atom, iodine atom etc.) can be performed according to the following method.

For example, about 1–3 equivalents, preferably about 1.2–2 equivalents, of tertiary amine, such as triethylamine and the like, and about 1–3 equivalents, preferably about 1.1–2 equivalents, of sulfonyl halide of the formula (27) (preferably methanesulfonyl chloride) are added to 4-methyl-4-nitropentanol in a suitable solvent, such as methylene chloride and the like, and the mixture is stirred at about room temperature –0° C. for 30 min–2 h, after which the reaction mixture is extracted to give 4-methyl-4-nitropentanol sulfonate of the formula (28). The obtained 4-methyl-4-nitropentanol sulfonate is generally isolated and/or purified before use by a conventional method such as crystallization, chromatography and the like.

Then, 4-methyl-4-nitropentanol sulfonate of the formula (28) is reacted with alkali metal halide to give 4-methyl-4-nitropentyl halide of the formula (29). Examples of preferable alkali metal halide include sodium iodide and sodium bromide. For example, about 1–10 equivalents, preferably about 4–5 equivalents, of alkali metal halide is added to 4-methyl-4-nitropentanol sulfonate of the formula (28) in a suitable solvent, such as acetone and the like, and the mixture is stirred at about 0° C.–30° C., preferably about 15° C.–25° C. for about 6–24 h, preferably about 10–12 h, after which the reaction mixture is concentrated (or evaporated) and extracted to give 4-methyl-4-nitropentyl halide of the formula (29). The obtained 4-methyl-4-nitropentyl halide can be isolated and/or purified by a conventional method, such as chromatography and the like, but generally, can be used in the next step without isolation and/or purification.

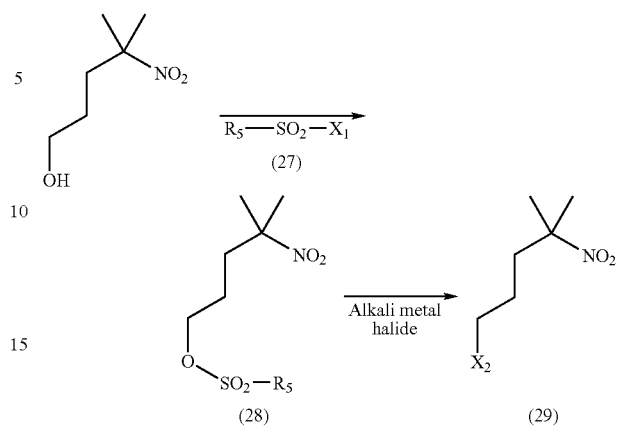

wherein $R_5$ is alkyl group having 1 to 3 carbon atoms or phenyl group optionally having a substituent (preferably alkyl group having 1 to 3 carbon atoms) and $X_1$ and $X_2$ are halogen atoms.

(iv) 4-Methyl-4-nitropentane derivative of the formula (6) (preferably 4-methyl-4-nitropentyl halide of the formula (29)) and 2-acetylaminomalonic diester of the formula (7) are reacted to give 2-acetylamino-2-(4-methyl-4-nitropentyl)malonic diester (racemate) of the aforementioned formula (8).

As 2-acetylaminomalonic diester of the formula (7), 2-acetamidomalonic acid diethyl ester wherein $R_2$ and $R_3$ are ethyl groups is particularly preferably used. For example, sodium ethoxide and 2-acetamidomalonic diester are dissolved in a suitable solvent, such as ethanol and the like, and 4-methyl-4-nitropentyl derivative is added. The mixture is reacted at about 50° C.—refluxing temperature for about 3–24 h. The reaction mixture is concentrated (or evaporated) and extracted to give 2-acetylamino-2-(4-methyl-4-nitropentyl)malonic diester (racemate) of the formula (8) (Tetrahedron, 1985, 41 (22), 5307–5311). The obtained 2-acetylamino-2-(4-methyl-4-nitropentyl)malonic diester (racemate) can be isolated and/or purified by a conventional method, such as chromatography and the like, but generally, can be used in the next step without isolation and/or purification.

(v) Alkali, such as potassium hydroxide and the like, is added to 2-acetylamino-2-(4-methyl-4-nitropentyl)malonic diester of the formula (8) in a mixed solvent of a water soluble solvent, such as ethanol and the like, and water, and the mixture is refluxed under heating to give 2-acetylamino-2-(4-methyl-4-nitropentyl)malonic acid. Thereto is added an acid, such as hydrochloric acid, sulfuric acid and the like, and the mixture is subjected to decarboxylation. The reaction mixture is concentrated by crystallization, or extracted to give 2-acetylamino-6-methyl-6-nitroheptanoic acid (racemate) of the formula (9) (Journal of Medicinal Chemistry, 1999, 42, 305–311). The obtained 2-acetylamino-6-methyl-6-nitroheptanoic acid (racemate) is generally isolated and/or purified before use by a conventional method, such as crystallization, chromatography and the like.

(vi) Acylase is made to act on 2-acetylamino-6-methyl-6-nitroheptanoic acid (racemate) of the formula (9) to give optically active 2-amino-6-methyl-6-nitroheptanoic acid of the formula (1). Acylase is not particularly limited, and conventionally available acylase (e.g., acylase manufactured by Amano Enzyme Inc.) and the like can be used. For example, L-acylase is added to an aqueous solvent adjusted to pH 5–10, preferably 6–9, containing 2-acetylamino-6-methyl-6-nitroheptanoic acid (racemate), and the mixture is preferably stirred at 30° C.–40° C. for about 3 h–2 days. The pH is adjusted to about 1–3 to precipitate unreacted D-enantiomer of the formula (9). After separation by filtration, the mother liquor is concentrated to dryness to give L-enantiomer of 2-amino-6-methyl-6-nitroheptanoic acid. When D-acylase is used here, D-enantiomer of 2-amino-6-methyl-6-nitroheptanoic acid can be obtained (*Journal of Medicinal Chemistry*, 1999, 42, 305–311).

As a different method, 2-acetylamino-6-methyl-6-nitroheptanoic acid (racemate) is treated with D-acylase to deacetylate D-enantiomer and unreacted L-enantiomer is crystallized under acidic conditions. The L-enantiomer of 2-amino-6-methyl-6-nitroheptanoic acid can be also obtained by separation of crystals, refluxing under heating in an acidic aqueous solution, deacetylation and concentration to dryness.

The obtained optically active 2-amino-6-methyl-6-nitroheptanoic acid can be isolated and/or purified by a conventional method, such as crystallization, chromatography and the like, but generally, can be used in the next step without isolation and/or purification.

The route (II) is explained in the following.

(vii) The method for producing 4-methyl-4-nitropentanal is exemplified by the following two methods.

(vii-1) Acrylonitrile and 2-nitropropane are reacted in the presence of hexadecyltrimethyl ammonium chloride in an aqueous alkali solvent such as aqueous sodium hydroxide solution and the like. Then, the reaction mixture is extracted to give 4-methyl-4-nitrovaleronitrile (*European Journal of Organic Chemistry* (1998), (2), 355–357). The obtained 4-methyl-4-nitrovaleronitrile can be isolated and/or purified by a conventional method, such as crystallization, chromatography and the like, but generally, can be used in the next step without isolation and/or purification.

4-Methyl-4-nitrovaleronitrile is reduced in a suitable solvent, such as methylene chloride and the like, with a reducing agent, such as diisobutylaluminum hydride and the like, at about 0° C. to −78° C., preferably from about −40° C. to −60° C., and treated with an acid, such as hydrochloric acid, sulfuric acid and the like, after which extracted to give 4-methyl-4-nitropentanal. The obtained 4-methyl-4-nitropentanal can be isolated and/or purified by a conventional method, such as distillation, chromatography and the like, but generally, can be used in the next step without isolation and/or purification.

(vii-2) It is also possible to obtain 4-methyl-4-nitropentanal by adding 2-nitropropane and acrolein to a liquid in which methanol and metallic sodium have been dissolved (see JP-A-01-305056). The obtained 4-methyl-4-nitropentanal can be isolated and/or purified before use by a conventional method, such as distillation, chromatography and the like.

(viii) Then, 4-methyl-4-nitropentanal and hydantoin are reacted to give 5-(4-methyl-4-nitropentylidene)hydantoin (see JP-A-11-140076).

For example, 4-methyl-4-nitropentanal and hydantoin are refluxed under heating in a mixed solvent of water soluble solvent, such as acetonitrile, isopropyl alcohol and the like, and water in the presence of a base, such as sodium carbonate, potassium carbonate and the like, preferably for about 3–5 days. Extraction thereafter gives 5-(4-methyl-4-nitropentylidene)hydantoin.

In this reaction, 5-(1-hydroxy-4-methyl-4-nitropentyl)hydantoin is generated as an intermediate product which is ultimately converted to the objective 5-(4-methyl-4-nitropentylidene)hydantoin.

It is also possible to obtain the objective 5-(4-methyl-4-nitropentylidene)hydantoin by isolating 5-(1-hydroxy-4-methyl-4-nitropentyl)hydantoin, protecting a hydroxyl group with methanesulfonyl chloride and the like to give 5-(1-methanesulfonyloxy-4-methyl-4-nitropentyl)hydantoin and the like, which is then treated with a base such as 1,8-diazabicyclo[5.4.0]undec-7-ene (DBU) and the like.

The obtained 5-(4-methyl-4-nitropentylidene)hydantoin can be isolated and/or purified by a conventional method, such as crystallization, chromatography and the like, but generally, can be used in the next step without isolation and/or purification.

(viv) 5-(4-Methyl-4-nitropentylidene)hydantoin is reduced with a transition metal catalyst (such as palladium) and the like to give 5-(4-methyl-4-nitropentyl)hydantoin. For example, 5-(4-methyl-4-nitropentylidene)hydantoin is reacted with hydrogen gas upon addition of palladium-carbon (generally 0.1–5 mol %, preferably 0.5–2 mol %) in a mixed solvent of a water soluble solvent, such as methanol, ethanol and the like, and water for 1–12 h, preferably 2–5 h. The reaction solvent is concentrated to dryness to give 5-(4-methyl-4-nitropentyl)hydantoin. The obtained 5-(4-methyl-4-nitropentyl)hydantoin can be isolated and/or purified by a conventional method, such as chromatography and the like, but generally, can be used in the next step without isolation and/or purification.

(x) 5-(4-Methyl-4-nitropentyl)hydantoin is hydrolyzed with alkali to give 2-amino-6-methyl-6-nitroheptanoic acid (see JP-A-11-140076). For example, 5-(4-methyl-4-nitropentyl)hydantoin is hydrolyzed in an aqueous solution preferably in the presence of 1–3 equivalents of alkali, such as sodium hydroxide, potassium hydroxide, sodium carbonate, potassium carbonate, calcium hydroxide, barium hydroxide and the like, relative to 5-(4-methyl-4-nitropentyl)hydantoin generally at 20–200° C., preferably 100–150° C. The reaction mixture is concentrated to dryness to give 2-amino-6-methyl-6-nitroheptanoic acid. The obtained 2-amino-6-methyl-6-nitroheptanoic acid can be isolated and/or purified by a conventional method, such as crystallization, chromatography and the like, but generally, can be used in the next step without isolation and/or purification.

(xi) The amino group of 2-amino-6-methyl-6-nitroheptanoic acid is acylated to give 2-acylamino-6-methyl-6-nitroheptanoic acid (racemate) of the formula (13) (see JP-A-11-140076). For example, 2-amino-6-methyl-6-nitroheptanoic acid is acylated in an aqueous solution adjusted to a pH higher than pH 7, preferably pH 8–11, preferably using 1–2 equivalents of acyl halide, such as acetyl chloride, benzoyl chloride and the like, or acid anhydride, such as acetic anhydride, benzoic anhydride and the like, generally at 0–80° C., preferably 0–30° C., to give 2-acylamino-6-methyl-6-nitroheptanoic acid (racemate). The obtained 2-acylamino-6-methyl-6-nitroheptanoic acid is isolated and/or purified before use by a conventional method such as crystallization, chromatography and the like.

(xii) Acylase is made to act on 2-acylamino-6-methyl-6-nitroheptanoic acid obtained as mentioned above according to the aforementioned method to give optically active 2-amino-6-methyl-6-nitroheptanoic acid of the formula (1).

The optically active 2-amino-6-methyl-6-nitroheptanoic acid of the formula (1) can be also produced by the following route (III). That is, 5-(4-methyl-4-nitropentyl)hydantoin of the formula (11) is enantio-selectively hydrolyzed using at least one member selected from the group consisting of a microorganism, a treated product thereof, hydantoinase and N-carbamyl-amino-acid hydrolase to give optically active 2-amino-6-methyl-6-nitroheptanoic acid of the formula (1) or a salt thereof.

The route (III) is explained in the following.

The optically active 2-amino-6-methyl-6-nitroheptanoic acid of the formula (1) can be also produced by enantio-selectively hydrolyzing 5-(4-methyl-4-nitropentyl)hydantoin of the formula (11) using at least one member selected from the group consisting of a microorganism, a treated product thereof, hydantoinase and N-carbamyl-amino-acid hydrolase.

The microorganism, and the origin of the treated product of a microorganism, hydantoinase and N-carbamyl-amino-acid hydrolase to be used here are preferably bacteria of the genus *Agrobacterium*, the genus *Bacillus* or the genus *Microbacterium*.

The microorganism, and the origin of the treated product of a microorganism, hydantoinase and N-carbamyl-amino-acid hydrolase to be used here are preferably bacteria of the genus *Agrobacterium*, and the optically active 2-amino-6-methyl-6-nitroheptanoic acid or a salt thereof is preferably D-2-amino-6-methyl-6-nitroheptanoic acid or a salt thereof.

Further, the microorganism, and the origin of the treated product of a microorganism, hydantoinase and N-carbamyl-amino-acid hydrolase to be used here are preferably bacteria of the genus *Microbacterium* or the genus *Bacillus*, and the optically active 2-amino-6-methyl-6-nitroheptanoic acid or a salt thereof is preferably L-2-amino-6-methyl-6-nitroheptanoic acid or a salt thereof.

5-(4-Methyl-4-nitropentyl)hydantoin of the formula (11) can be prepared by a method of the route (II). The 5-(4-methyl-4-nitropentyl)hydantoin to be prepared may be purified or isolated by a conventional method or contained in a reaction mixture. 5-(4-Methyl-4-nitropentyl)hydantoin may be a mixture of a D-enantiomer and an L-enantiomer, or either of them. In the case of a mixture of a D-enantiomer and an L-enantiomer, the mixing ratio is optional.

The microorganism, a treated product thereof, hydantoinase and N-carbamyl-amino-acid hydrolase to be used here may be any as long as they can hydrolyze 5-(4-methyl-4-nitropentyl)hydantoin enantio-selectively.

The enantio-selective hydrolysis is a reaction capable of affording optically active 2-amino-6-methyl-6-nitroheptanoic acid of the formula (1) or a salt thereof by hydrolysis of 5-(4-methyl-4-nitropentyl)hydantoin of the formula (11), wherein either D-enantiomer or L-enantiomer of 2-amino-6-methyl-6-nitroheptanoic acid or a salt thereof is generated.

The microorganism, a treated product thereof and hydantoinase include those that can act on 5-(4-methyl-4-nitropentyl)hydantoin, and enantio-selectively hydrolyze same, by which to generate optically active N-carbamyl-2-amino-6-methyl-6-nitroheptanoic acid, which is specifically N-carbamyl-L-2-amino-6-methyl-6-nitroheptanoic acid or N-carbamyl-D-2-amino-6-methyl-6-nitroheptanoic acid. This is because, even when the microorganism and the treated product thereof do not have an activity to enantio-selectively convert N-carbamyl-2-amino-6-methyl-6-nitroheptanoic acid to 2-amino-6-methyl-6-nitroheptanoic acid, or even when hydantoinase alone catalyzes an enantio-selective reaction, optically active 2-amino-6-methyl-6-nitroheptanoic acid can be produced in a high yield while maintaining optical activity by continuously applying an enzymatic hydrolysis treatment using N-carbamyl-amino-acid hydrolase or a substance containing this enzyme, or by applying a chemical hydrolysis treatment by nitrous acid.

The microorganism, a treated product thereof and N-carbamyl-amino-acid hydrolase include those that can act on N-carbamyl-2-amino-6-methyl-6-nitroheptanoic acid, and enantio-selectively hydrolyze same, by which to produce optically active 2-amino-6-methyl-6-nitroheptanoic acid. This is because, even when the microorganism and the treated product thereof do not have an activity to enantio-selectively convert 5-(4-methyl-4-nitropentyl)hydantoin to N-carbamyl-2-amino-6-methyl-6-nitroheptanoic acid, or even when N-carbamyl-amino-acid hydrolase alone catalyzes an enantio-selective reaction, optically active 2-amino-6-methyl-6-nitroheptanoic acid can be produced in a high yield by previously applying an enzymatic hydrolysis treatment using hydantoinase or a substance containing this enzyme, or by applying a chemical hydrolysis treatment.

Therefore, any microorganism or any treated product thereof can be used in the present invention as long as it contains hydantoinase that can act on 5-(4-methyl-4-nitropentyl)hydantoin and perform enantio-selective hydrolysis, thereby to generate optically active N-carbamyl-2-amino-6-methyl-6-nitroheptanoic acid. Furthermore, any microorganism or any treated product thereof can be used even if it contains hydantoinase without enantio-selectivity, only if it contains enantio-selective N-carbamyl-amino-acid hydrolase that can enantio-selectively hydrolyze the generated N-carbamyl-2-amino-6-methyl-6-nitroheptanoic acid, thereby to produce optically active 2-amino-6-methyl-6-nitroheptanoic acid.

The microorganism as referred to in the present invention can be cultured by any culture method, such as liquid culture, solid culture and the like, as long as it maintains the required ability. Both the culture broth itself and viable bacterial cells harvested from the culture broth can be used. The microorganism of the present invention may be a strain newly isolated from nature, such as soil and plant, or may be a strain artificially bred by mutagen treatment, recombinant DNA technology and the like.

For culture of microorganism in the present invention, a medium generally employed in this field is used, such as a medium containing carbon source, nitrogen source, mineral, trace metal salts, vitamin group and the like. Depending on the kind of microorganism and culture conditions, a 5-substituted hydantoin compound such as 5-indolylmethylhydantoin or 5-isopropylhydantoin may be added to the medium in a proportion of about 0.05–1.0 g/dl to promote the activity to produce optically active 2-amino-6-methyl-6-nitroheptanoic acid. To increase permeability of 5-(4-methyl-4-nitropentyl)hydantoin (substrate) into a bacterial cell, a surfactant, such as Triton X and Tween, and/or an organic solvent, such as toluene and xylene, can be used. Referring to the specific substances to be used as the components of the above-mentioned medium, for example, the carbon source is not subject to any particular limitation as long as the microorganism to be used can consume, and glucose, sucrose, fructose, glycerol, maltose, acetic acid and a mixture of these can be used. As the nitrogen source, ammonium sulfate, ammonium chloride, urea, yeast extract, meat extract, corn steep liquor, casein hydrolysate and a mixture of these can be used. A concrete medium composition is, for example, a medium containing glucose 0.5%, ammonium sulfate 0.5%, powder yeast extract 1.0%, peptone 1.0%, $KH_2PO_4$ 0.1%, $K_2HPO_4$ 0.3%, $MgSO_4.7H_2O$ 0.05%, $FeSO_4.7H_2O$ 0.001% and $MnSO_4.5H_2O$ 0.001% (pH 7.0) and the like.

The culture temperature is generally within the range where the microorganism to be used can grow, which is 20–45° C., preferably 25–37° C. The pH of the medium is adjusted to 3–11, preferably 4–8. The aeration condition is aerobic or anaerobic and set suitably for the growth of the microorganism to be used, with preference given to aerobic condition. The culture time is not particularly limited as long as optically active 2-amino-6-methyl-6-nitroheptanoic acid is generated efficiently. It is generally about 12–144 h, preferably about 24–96 h.

The microorganism to be used in the present invention is preferably a microorganism belonging to the genus *Agrobacterium* for producing (R)-2-amino-6-methyl-6-nitroheptanoic acid, and a microorganism belonging to the genus *Microbacterium* or the genus *Bacillus* for producing (S)-2-amino-6-methyl-6-nitroheptanoic acid.

Specific example of the microorganism used for producing, for example, (R)-2-amino-6-methyl-6-nitroheptanoic acid is *Agrobacterium* sp. AJ11220 strain (formerly classified under *Pseudomonas hydantoinophilum*). The *Agrobacterium* sp. AJ11220 strain was deposited at the then National Institute of Bioscience and Human-Technology, Agency of Industrial Science and Technology, Ministry of International Trade and Industry (now International Patent organism Depositary, National Institute of Advanced Industrial Science and Technology, an Independent Administrative Institution under Ministry of Economy, Trade and Industry) on Dec. 20, 1977 under the accession number of FERM-P4347, and then transferred to an international deposition under the Budapest Treaty on Jun. 27, 2001, and received a accession number of FERM BP-7645. For the production of (S)-2-amino-6-methyl-6-nitroheptanoic acid, moreover, *Microbacterium liquefaciens* AJ3940 (formerly classified under *Aureobacterium liquefaciens* still formerly classified under *Flavobacterium* sp.), *Bacillus* sp. AJ12299 can be mentioned. *Microbacterium liquefaciens* AJ3940 strain was deposited on Jun. 27, 1975, and *Bacillus* sp. AJ12299 strain was deposited on Jul. 5, 1986, at the then National Institute of Bioscience and Human-Technology, Agency of Industrial Science and Technology, Ministry of International Trade and Industry (now International Patent organism Depositary, National Institute of Advanced Industrial Science and Technology, an Independent Administrative Institution under Ministry of Economy, Trade and Industry) under the accession number of FERM-P3135 and FERM-P8837, respectively, and then transferred to an international deposition under the Budapest Treaty both on Jun. 27, 2001, and received a accession number of FERM BP-7644 and FERM BP-7646, respectively.

The treated product of microorganism as referred to in the present invention is obtained by subjecting the microorganism to be used in the present invention to a physical treatment using, for example, ultrasonication, glass beads, French press, lyophillization and the like; enzymatic treatment using lytic enzyme etc.; chemical treatment using an organic solvent, surfactant etc.; and the like. The treated product of microorganism in the present invention may be a culture broth of a microorganism or viable bacterial cells, that underwent such treatments, as long as it has the required ability. Furthermore, a crude fractionation enzyme or purification enzyme prepared by a conventional method (liquid chromatography, ammonium sulfate fractionation etc.) from a substance that underwent such treatments may be used as the treated product of microorganism in the present invention, as long as it has the required ability.

The origin of the treated product of microorganism is preferably, for example, a microorganism belonging to the genus *Agrobacterium* for producing (R)-2-amino-6-methyl-6-nitroheptanoic acid, and a microorganism belonging to the genus *Microbacterium* or the genus *Bacillus* for producing (s)-2-amino-6-methyl-6-nitroheptanoic acid.

The origin of the treated product of microorganism means the microorganism before the treatment. However, the origin of the treated product of microorganism obtained by treating a transformant prepared by isolating a gene of hydantoinase from a microorganism having a hydantoinase activity, or isolating a gene of N-carbamyl-amino-acid hydrolase from a microorganism having an N-carbamyl-amino-acid hydrolase activity, and transforming a microorganism with the gene is the microorganism from which the gene was isolated.

A hydantoinase that hydrolyzes a hydantoin compound enantio-selectively can be obtained as follows. For example, bacteria having D-hydantoinase that produces N-carbamyl-D-amino acid is known to be the bacteria of the genus *Bacillus* having a heat resistant enzyme. Thus, a fraction containing hydantoinase or hydantoinase can be prepared from, for example, *Bacillus stearothermophilus* ATCC31195 and the like [*Appl. Microbiol. Biotechnol.*, Vol. 43, p. 270 (1995)]. The ATCC31195 strain is available from the American Type Culture Collection (address: 12301 Parklawn Drive, Rockville, Md. 20852, United States of America). The L-hydantoinase known to specifically act on an L-enantiomer of hydantoin compound is known to exist in, for example, the above-mentioned *Bacillus* sp. AJ12299 strain (JP-A-63-24894).

A hydantoinase without enantio-selectivity is known to exist in *Microbacterium liquefaciens* AJ3912 (formerly classified under *Aureobacterium liquefaciens* still formerly classified under *Flavobacterium* sp.) and the above-mentioned *Microbacterium liquefaciens* AJ3940 (JP-B-56-008749), as well as, for example, *Arthrobacter aurescens* [*J. Biotechnol.*, vol. 61, p. 1, (1998)]. The AJ3912 strain was deposited at the then National Institute of Bioscience and Human-Technology, Agency of Industrial Science and Technology, Ministry of International Trade and Industry (now International Patent Organism Depositary, National Institute of Advanced Industrial Science and Technology, an Independent Administrative Institution under Ministry of Economy, Trade and Industry) on Jun. 27, 1975 under the deposit No. of FERM-P3133, and then transferred to an international deposition under the Budapest Treaty on Jun. 27, 2001, and received a accession number of FERM BP-7643.

The N-carbamyl-amino-acid hydrolase that hydrolyzes N-carbamyl-amino acid in a D-enantiomer-selective manner is known to exist in the above-mentioned *Agrobacterium* sp. AJ11220 strain (JP-B-56-003034). The N-carbamyl-amino-acid hydrolase that hydrolyzes N-carbamyl-amino acid in an L-enantiomer-selective manner is known to exist in the above-mentioned *Microbacterium liquefaciens* AJ3912 (JP-B-56-008749) and *Bacillus* sp. AJ12299.

The preferable origin of hydantoinase and N-carbamyl-amino-acid hydrolase is, for example, a microorganism belonging to the genus *Agrobacterium* for producing (R)-2-amino-6-methyl-6-nitroheptanoic acid (D-enantiomer), and a microorganism belonging to the genus *Microbacterium* or the genus *Bacillus* for producing (S)-2-amino-6-methyl-6-nitroheptanoic acid (L-enantiomer).

By the origin of hydantoinase is meant the resources from which the hydantoinase is obtained. The origin of hydantoinase obtained by lysis of cells of a microorganism having a hydantoinase activity is this microorganism. However, the origin of hydantoinase obtained from a transformant obtained by isolating a hydantoinase gene from a microorganism having a hydantoinase activity and transforming a microorganism with the gene is the microorganism from which the gene was isolated.

By the origin of N-carbamyl-amino-acid hydrolase is meant the resources from which the N-carbamyl-amino-acid hydrolase is obtained. The origin of N-carbamyl-amino-acid hydrolase obtained by lysis of cells of a microorganism having an N-carbamyl-amino-acid hydrolase activity is this microorganism. However, the origin of N-carbamyl-amino-acid hydrolase obtained from a transformant obtained by isolating an N-carbamyl-amino-acid hydrolase gene from a microorganism having an N-carbamyl-amino-acid hydrolase activity and transforming a microorganism with the gene is the microorganism from which the gene was isolated.

The 5-(4-methyl-4-nitropentyl)hydantoin to be the substrate is added to a reaction system containing bacterial cell separated after culture of the microorganism, a treated product thereof, hydantoinase or N-carbamyl-amino-acid hydrolase, all at once or intermittently or continuously within the concentration range where the production of optically active 2-amino-6-methyl-6-nitroheptanoic acid is not limited. The method for addition may be direct addition into the culture of the microorganism. An organic solvent or a surfactant may be added to the reaction system together with the substrate for the purpose of increasing the solubility or promoting dispersion. In addition, medium components, such as carbon source and nitrogen source, may be added to the reaction system together with the substrate for the purpose of continuing or promoting the metabolism of the microorganism.

When a microorganism, a treated product thereof, hydantoinase or N-carbamyl-amino-acid hydrolase is subjected to a reaction, it may be included in carrageenan gel or polyacrylamide, or immobilized on a membrane of polyether sulfone, regenerated cellulose and the like.

The reaction system of the present invention is obtained by adjusting a reaction mixture containing a hydantoin compound and a microorganism, a treated product thereof, hydantoinase or N-carbamyl-amino-acid hydrolase at a suitable temperature of 25–40° C. and standing or stirring the mixture for 8 h–5 days while maintaining pH 5–9.

The amount of (R)- or (S)-2-amino-6-methyl-6-nitroheptanoic acid in the culture broth or the reaction mixture can be measured quickly according to a known method. For example, high performance liquid chromatography using an optical resolution column such as "CROWNPAK CR(+)" manufactured by DAICEL CHEMICAL INDUSTRIES, LTD. can be applied. In this way, (R)- or (S)-2-amino-6-methyl-6-nitroheptanoic acid accumulated in the culture broth or the reaction mixture can be harvested from the culture broth or the reaction mixture by a conventional method and used. Harvesting from the culture broth or the reaction mixture can be done according to a method generally used in the pertinent field for this purpose, such as filtration, centrifugation, concentration in vacuo, ion-exchange or adsorption chromatography, crystallization and the like, which may be combined as appropriate.

The production method of the present invention shown in the following is now explained.

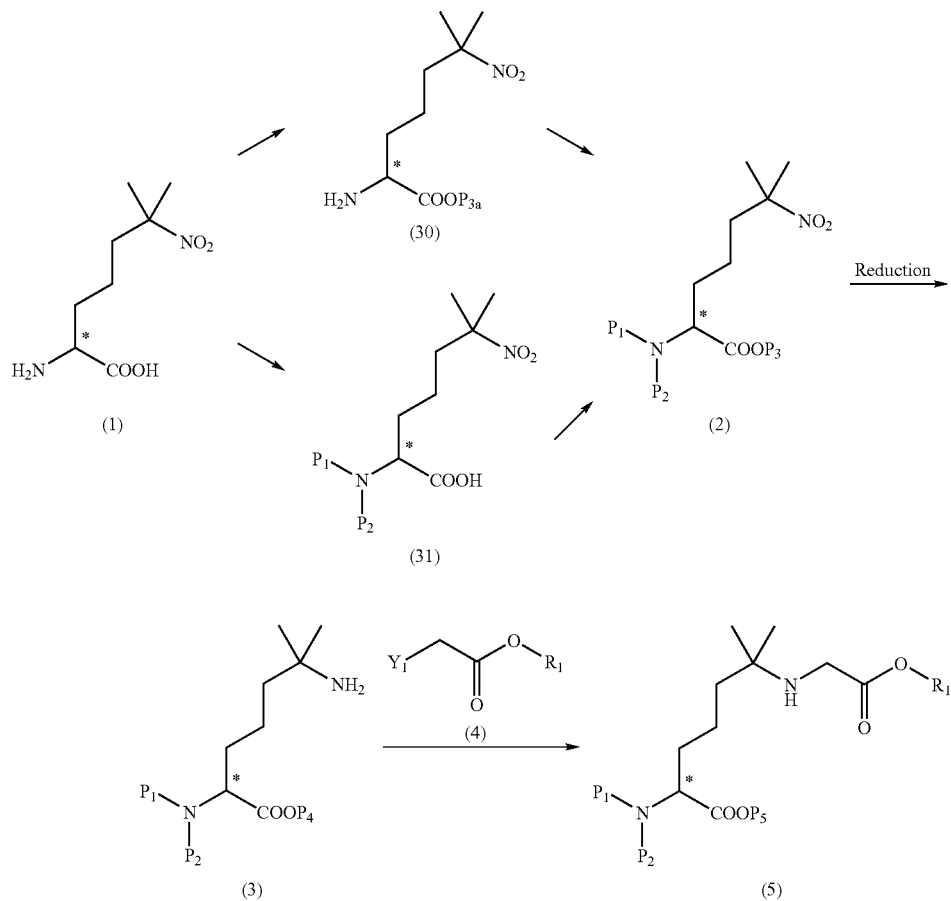

wherein *, $P_1$, $P_2$, $P_3$, $P_{3a}$, $P_4$, $P_5$, $Y_1$ and $R_1$ are as defined above.

A method wherein the amino group or amino group and carboxyl group of the optically active 2-amino-6-methyl-6-nitroheptanoic acid of the formula (1) are protected by a protecting group to produce an optically active amino acid derivative of the formula (2) is explained first.

The protection by a protecting group may be first applied to either amino group or carboxyl group. The carboxyl group is not necessarily protected during reduction, and the protection may not be applied up to the compound of the formula (5), depending on the purpose. When protected, the protection before reduction is preferable, but protection in an optional process thereafter is also acceptable. The claims of the present invention encompass such mode of the process.

The amino group can be protected by applying an amino group-protecting reagent, such as alkoxycarbonylating reagent, acylating reagent, sulfonylating reagent and the like, where necessary, in the presence of a base.

For example, a compound of the formula (1) or the formula (30) is dissolved in advance in a suitable solvent by adding, where necessary, a suitable base and an amino group-protecting reagent, such as alkoxycarbonylating reagent, acylating reagent, sulfonylating reagent and the like.

The amino group-protecting reagent is not particularly limited, and any compound containing a functional group, such as alkoxycarbonyl group, acyl group, sulfonyl group and the like, can be used for introducing any substituent, not to mention reagents generally used for peptide synthesis.

Examples of the amino group-protecting reagent include alkoxycarbonylating reagent such as methoxycarbonyl chloride, ethoxycarbonyl chloride, t-butoxycarbonyl chloride, benzyloxycarbonyl chloride, di-t-butyldicarbonate, tetrahydrofuran-3-yloxycarbonyl chloride and the like; acylating reagent such as acetic anhydride, acetyl chloride, benzoyl chloride, trifluoroacetic anhydride and the like; sulfonylating reagent such as methanesulfonyl chloride, trifluoromethanesulfonyl chloride, benzenesulfonyl chloride, p-toluenesulfonyl chloride and the like; and the like.

Particularly, protection with a t-butoxycarbonyl group is preferable. In this case, a preferable protecting reagent is di-t-butyldicarbonate.

The amino group-protecting reagent is used in an amount of generally 1–1.5 equivalents, preferably 1.1–1.3 equivalents, relative to the compound to be protected. Similarly, the base is used in an amount of generally 1–3 equivalents, preferably 1.5–2 equivalents.

The solvent to be used for the protection of amino group may be water, methanol, ethanol, tetrahydrofuran, ethyl acetate, dichloromethane, chloroform, toluene and the like, a mixed solvent of these and the like, and a suitable solvent can be used depending on the reagent.

Examples of the base include pyridine, triethylamine, sodium hydroxide, potassium hydroxide, sodium carbonate, potassium carbonate, sodium hydrogen carbonate, potassium hydrogen carbonate, disodium hydrogenphosphate, dipotassium hydrogenphosphate and the like. For the compound of the formula (1), sodium hydroxide and potassium hydroxide are particularly preferable, and for the compound of the formula (30), sodium hydrogen carbonate and potassium hydrogen carbonate are preferable.

The reaction time varies depending on the reagent to be used and the reaction temperature. When t-butoxycarbonylation is applied using di-t-butyldicarbonate, the reaction ends in several minutes to about 2 h at 40° C. and several minutes to about 10 h at room temperature.

The carboxyl group can be generally protected by esterification. In the case of a compound of the formula (1), for example, alcohol and thionyl chloride are mixed in advance and the compound of the formula (1) is added for reaction. In the case of a compound of the formula (31), for example, an esterifying agent, such as dimethylformamide dimethylacetal and the like, is used or a base and an alkylating agent are used to esterify carboxyl group.

The solvent to be used for esterification of carboxyl group may be methanol, ethanol, t-butanol, benzyl alcohol, toluene, tetrahydrofuran, dichloromethane and the like or a mixed solvent of these and the like. A suitable solvent can be used according to the ester group to be introduced.

When the carboxyl group of the compound of the formula (1) is esterified, for example, generally, 2–3 equivalents of hydrogen chloride gas, 1–2 equivalents of acetyl chloride, or 1–2 equivalents of p-toluenesulfonic acid is added into alcohol (for example, methanol to give methyl ester) to introduce an ester group.

Alternatively, alcohol and about 1–1.2 equivalents of thionyl chloride are reacted and a compound of the formula (1) is added. While the reaction time varies depending on the reagent to be used, reaction temperature and the like, when methanol-thionyl chloride is used for methyl esterification, for example, the reaction completes in generally about 3–5 h at 60° C.

In the case of a compound of the formula (31), for example, about 1.5–2.5 equivalents of esterifying agent such as dimethylformamide dimethylacetal and the like is used for esterification. It is also possible to use a method wherein about 1–1.5 equivalents of alkyl halide (for example, methyl iodide and benzyl bromide) is reacted in the presence of about 1–1.5 equivalents of a base (for example, amine such as cyclohexylamine and the like, alkali metal salt such as cesium carbonate and the like) for protection. While the reaction time varies depending on the reagent to be used and the reaction temperature, when methyl esterification is conducted in dichloromethane using dimethylformamide dimethylacetal, the reaction completes in generally about 20–24 h at room temperature.

A step for producing optically active 6,6-dimethyl lysine derivative of the formula (3) or a salt thereof by reducing the nitro group of the optically active amino acid derivative of the formula (2) is explained in the following.

The nitro group can be reduced in a suitable alcohol solvent, such as methanol, ethanol, isopropyl alcohol and the like or a mixed solvent of such alcohol and water, preferably by [1] reduction using a combination of metal and metallic sulfate or metallic chloride; [2] catalytic reduction using a combination of a transition metal catalyst and metallic sulfate or metallic chloride; or [3] catalytic reduction using a transition metal catalyst.

The [1] reduction using a combination of metal and metallic sulfate or metallic chloride is explained in the following.

A preferable metal includes iron, zinc and the like. A preferable metallic sulfate includes ferrous sulfate, copper sulfate, sodium hydrogensulfate and the like. A preferable metallic chloride includes zinc chloride, cobalt chloride and the like. The metallic sulfate and metallic chloride may be mixed for use.

A particularly preferable combination is iron and ferrous sulfate and/or sodium hydrogensulfate.

For example, the reduction can be conducted by the use of 1–40 equivalents of iron and 1–20 equivalents of ferrous sulfate (and/or sodium hydrogensulfate), preferably 20–30 equivalents of iron and 10–15 equivalents of ferrous sulfate (and/or sodium hydrogensulfate), relative to the optically active amino acid derivative of the formula (2) and stirring them in the above-mentioned solvent preferably at a temperature of from room temperature to 50° C. The pressure may be the atmospheric pressure. The time necessary for the reduction varies depending on the metal, metallic sulfate and the like to be added, but it is generally 6–72 h.

The [2] catalytic reduction using a combination of a transition metal catalyst and metallic sulfate or metallic chloride is explained in the following.

A preferable transition metal catalyst is palladium catalyst, platinum catalyst and the like. Such transition metal catalyst can be used in the form of palladium-carbon, platinum hydroxide, platinum dioxide, platinum-carbon and the like.

A preferable metallic sulfate is ferrous sulfate, copper sulfate and the like. A preferable metallic chloride is zinc chloride, cobalt chloride and the like. The metallic sulfate and metallic chloride may be mixed for use.

A particularly preferable combination is palladium catalyst and ferrous sulfate.

For example, the reduction can be conducted by the use of generally 0.5–10 mol %, preferably 1–3 mol %, of a palladium catalyst and generally 1–10 equivalents of ferrous sulfate, preferably 2–5 equivalents of iron, relative to the optically active amino acid derivative of the formula (2) and stirring them in the above-mentioned solvent at a hydrogen pressure of generally 1–20 atm, preferably 1–5 atm, at a reaction temperature of generally from room temperature to 100° C., preferably from room temperature to 40° C. The time necessary for the reduction varies depending on the catalyst to be added, temperature, pressure and the like, but it is generally 3–48 h.

The [3] catalytic reduction using a transition metal catalyst is explained in the following.

A preferable transition metal catalyst is palladium catalyst, platinum catalyst and the like. These transition metal catalysts can be used in the form of palladium-carbon, platinum hydroxide, platinum dioxide, platinum-carbon and the like.

For example, the reduction can be conducted by the use of generally 0.5–10 mol %, preferably 1–3 mol %, of a palladium catalyst relative to the optically active amino acid derivative of the formula (2) and stirring them in the above-mentioned solvent at a hydrogen pressure of generally 10–30 atm, preferably 15–20 atm, at a reaction temperature of generally 50° C.–100° C., preferably 70° C.–90° C. The time necessary for the reduction varies depending on the catalyst to be added and the like, but it is generally 3–48 h.

The reduction [1] can be conducted at a relatively low temperature and low pressure (for example, ordinary temperature, atmospheric pressure) but requires a relatively large amount of metal such as iron and the like. The amount of the transition metal to be used for reduction [3] is relatively small but the reduction requires reaction at a relatively high temperature and a high pressure. The reduction [2] requires relatively small amounts of the transition metal and the like to be used and can be conducted at a relatively low temperature and, a low pressure (for example, ordinary temperature, atmospheric pressure), and therefore, industrially superior to the above-mentioned methods [1] and [3].

The reaction mixture containing the thus-obtained optically active 6,6-dimethyl lysine derivative of the formula (3) is concentrated (or evaporated) by concentration under reduced pressure and the like, and adjusted to about pH 8–9 with water and a base, such as sodium carbonate, sodium hydrogen carbonate and the like, and extracted with an organic solvent, such as ethyl acetate, toluene, dichloromethane and the like, or a mixed solvent, such as toluene-isopropyl alcohol and the like.

The organic solvent layer is evaporated by concentration under reduced pressure and the like to give an optically active 6,6-dimethyl lysine derivative. The derivative can be further purified by a conventional method such as chromatography and the like.

A step for producing an optically active lysine derivative of the formula (5) or a salt thereof by reacting an optically active 6,6-dimethyl lysine derivative of the formula (3) or a salt thereof and an acetate derivative of the formula (4) is explained in the following.

The acetate derivative of the formula (4) can be synthesized easily from an α-hydroxyacetate derivative. For example, trifluoromethanesulfonic anhydride is added to benzyl α-hydroxyacetate in dichloromethane in the presence of pyridine to give benzyl trifluoromethanesulfonyloxyacetate (*Angewandte Chemie* 1986, 98, 264). The α-halogenoacetate derivative is on the market from Sigma-Aldrich Japan K.K. and the like and can be obtained easily.

The 6,6-dimethyl lysine derivative of the formula (3) is dissolved in a suitable solvent and reacted with acetate derivative in the presence of a base. The solvent is exemplified by acetonitrile, methanol, ethanol, isopropyl alcohol, ethyl acetate, methyl t-butyl ether, toluene and the like. As the base, tertiary amine, such as triethylamine, diethylisopropylamine, diisopropylethylamine and the like, is used in an amount of generally 2–10 equivalents, preferably 3–4 equivalents relative to the 6,6-dimethyl lysine derivative. The acetate derivative is used in an amount of generally 1–2 equivalents, preferably about 1.2 equivalents. The mixture is stirred generally at 0° C.–40° C., preferably at room temperature, for generally about 12–48 h, preferably about 18–24 h. The reaction mixture is concentrated (or evaporated) by concentration under reduced pressure and the like, and extracted with an organic solvent such as ethyl acetate, toluene, dichloromethane and the like or a mixed solvent such as toluene-isopropyl alcohol and the like. Then, the organic solvent layer is evaporated under reduced pressure to give the optically active lysine derivative of the formula (5).

Alternatively, the optically active lysine derivative of the formula (5) is dissolved in a solvent such as tetrahydrofuran, dichloromethane, chloroform, acetone, acetonitrile and the like, to which are added an acid such as methanesulfonic acid, p-toluenesulfonic acid and the like in a proportion of generally 0.8–1.5 equivalents, preferably 1.0–1.1 equivalents, and a poor solvent, such as ethyl acetate, diethyl ether, petroleum ether, methyl tert-butyl ether, tert-butyl acetate, isopropyl acetate, hexane, cyclohexane, methylcyclohexane, heptane, toluene, xylene, methyl isobutyl ketone and the like, to allow precipitation (crystallization) of a salt, which salt is separated and dried to give crystals of a salt of the optically active lysine derivative of the formula (5).

Alternatively, the optically active lysine derivative of the formula (5) is dissolved in a solvent such as ethyl acetate, diethyl ether, petroleum ether, methyl tert-butyl ether, tert-butyl acetate, isopropyl acetate, hexane, cyclohexane, methylcyclohexane, heptane, toluene, xylene, methyl isobutyl ketone and the like, to which is added an acid such as methanesulfonic acid, p-toluenesulfonic acid and the like in a proportion of generally 0.8–1.5 equivalents, preferably 1.0–1.1 equivalents, to allow precipitation (crystallization) of a salt, which salt is separated and dried to give crystals of a salt of the optically active lysine derivative of the formula (5).

The present invention is explained in detail by referring to the examples. The present invention is not limited by these examples in any way.

REFERENCE EXAMPLE 1 methyl 4-methyl-4-nitropentanoate

2-Nitropropane (25 g, 0.28 mol) was dissolved in ethanol (140 ml) and methyl acrylate (25.3 ml, 0.28 mol) and potassium fluoride (1.63 g, 0.028 mol) were added. The mixture was refluxed under heating for 4 h. After cooling, ethanol was evaporated by concentration under reduced pressure, and the residue was extracted with ethyl acetate (100 ml) and water (50 ml). Ethyl acetate was evaporated under reduced pressure to give the objective compound (40.6 g, yield 82.5%).

$^1$H-NMR(CDCl$_3$) δ ppm: 1.60(s,6H), 2.22–2.38(m,4H), 3.70(s,3H)

REFERENCE EXAMPLE 2

4-methyl-4-nitropentanol

Methyl 4-methyl-4-nitropentanoate (17.5 g, 0.1 mol) was dissolved in ethanol (200 ml) and cooled to 5° C., after which sodium borohydride (7.55 g, 0.2 mol) was added. The mixture was stirred at room temperature for 1 h, and at 50° C. for 3 h. Water (100 ml) and hydrochloric acid were added to adjust the pH to 3, and ethanol was evaporated by concentration under reduced pressure. The residue was extracted with ethyl acetate (250 ml) and water (100 ml) and washed with saturated brine. Ethyl acetate was evaporated by concentration under reduced pressure to give the objective compound (14.7 g, yield 91.2%).

$^1$H-NMR(CDCl$_3$) δ ppm: 1.5(m,2H), 1.61(s,6H), 1.95–2.05(m,2H), 3.65(t,2H)

REFERENCE EXAMPLE 3

4-methyl-4-nitropentanol methanesulfonate

4-Methyl-4-nitropentanol (4.3 g, 29.2 mmol) was dissolved in methylene chloride (100 ml) and triethylamine (6.1 ml, 43.8 mmol) was added, which was followed by ice-cooling. Methanesulfonyl chloride (2.94 ml, 38.0 mmol) was added and the mixture was stirred for 1 h under ice-cooling. The mixture was washed with water (50 ml), 0.5 mol/L hydrochloric acid (50 ml), 5% aqueous sodium hydrogencarbonate solution (50 ml) and saturated brine (50 ml). Methylene chloride was evaporated by concentration under reduced pressure and the residue was subjected to crystallization with ethyl acetate (4 ml) and n-hexane (20 ml). After filtration, the residue was dried under reduced pressure at 40° C. to give the objective compound (6.17 g, yield 93.8%).

$^1$H-NMR(CDCl$_3$) δ ppm: 1.62(s,6H), 1.70–1.80(m,2H), 2.05(dd,2H), 3.06(s,3H), 4.23(t,2H) mass spectrum m/e: 243(M+NH$_4$+)

EXAMPLE 1

4-methyl-4-nitropentyl iodide

4-Methyl-4-nitropentanol methanesulfonate (3.38 g, 15 mmol) was dissolved in acetone (50 ml) and sodium iodide (8.7 g, 58 mmol) was added. The mixture was stirred overnight. Water (20 ml) was added and acetone was evaporated by concentration under reduced pressure. The residue was extracted with ethyl acetate (50 ml). The extract was washed with 5% aqueous sodium thiosulfate solution (20 ml) and saturated brine (20 ml), and ethyl acetate was evaporated by concentration under reduced pressure to give the objective compound (3.84 g, yield 99.6%).

$^1$H-NMR(CDCl$_3$) δ ppm: 1.60(s,6H), 1.74–1.86(m,2H), 2.02(dd,2H), 3.18(t,2H)

EXAMPLE 2 diethyl 2-acetylamino-2-(4-methyl-4-nitropentyl)malonate

20% Sodium ethoxide (3.74 g, 11 mmol) and diethyl 2-acetamidomalonate (2.39 g, 11 mmol) were dissolved in ethanol (10 ml). A solution of 4-methyl-4-nitropentyl iodide (2.57 g, 10 mmol) in ethanol (8 ml) was added and the mixture was refluxed under heating for 5 h. Ethanol was evaporated by concentration under reduced pressure and ethyl acetate (50 ml) was added. The mixture was washed with water (20 ml) and saturated brine (20 ml). Ethyl acetate was evaporated by concentration under reduced pressure and the residue was purified by silica gel column chromatography to give the objective compound (2.89 g, yield 83.4%).

$^1$H-NMR(CDCl$_3$) δ ppm: 1.00–1.14(m,2H), 1.25(t,6H), 1.54(s,6H), 1.89(dd,2H), 2.05(s,3H), 2.33(dd,2H), 1.44(q, 4H) mass spectrum m/e: 347(MH$^+$)

EXAMPLE 3

2-acetylamino-6-methyl-6-nitroheptanoic acid

Diethyl 2-acetylamino-2-(4-methyl-4-nitropentyl)malonate (193.5 g, 558.5 mmol) was dissolved in ethanol (270 ml), and potassium hydroxide (51 g, 781.9 mmol) was dissolved in water (250 ml) and added. The mixture was stirred at 90° C. for 1 h, and potassium hydroxide (51 g, 781.9 mmol) was dissolved in water (250 ml) and added. The mixture was stirred at the same temperature for 2 h. The mixture was cooled to 40° C. and concentrated hydrochloric acid was added to adjust the solution to pH 1.5, which solution was stirred overnight at 80° C. Ethanol was evaporated by concentration under reduced pressure and the residue was ice-cooled. The precipitated crystals were separated, and the obtained slurry was washed with ethyl acetate (200 ml) and dried under reduced pressure to give the objective compound (99.6 g, yield 72%).

$^1$H-NMR(CDCl$_3$) δ ppm: 1.23–1.44(m,2H), 1.57(s,6H), 1.66–1.78(m,2H), 1.91(t,2H), 2.04(s,3H), 4.53(dd,1H) mass spectrum m/e: 245(MH$^-$)

EXAMPLE 4

(S)-2-amino-6-methyl-6-nitroheptanoic acid

2-Acetylamino-6-methyl-6-nitroheptanoic acid (49.5 g, 200 mmol) was dissolved in water (246 ml) and 30% sodium hydroxide was added to adjust its pH to 8.87. L-Acylase (4.95 g) and anhydrous cobalt chloride (0.27 g) were added to adjust its pH to 9 and the mixture was stirred overnight at room temperature. Concentrated hydrochloric acid was added to adjust its pH to 1.5 and the mixture was ice-cooled. The precipitated crystals were separated by filtration and the filtrate was washed twice with a mixture (250 ml) of toluene-isopropyl alcohol (1:1) and the aqueous layer was concentrated under reduced pressure. Methanol (100 ml) was added for concentration and methanol (100 ml) was further added for concentration. As a result, the objective compound was obtained (20.5 g).

$^1$H-NMR(DMSO-d$_6$) δ ppm: 1.19–1.42(m,2H), 1.54(s, 6H), 1.68–1.76(m,2H), 1.86(t,2H), 3.53(t,1H)

EXAMPLE 5 methyl (S)-2-amino-6-methyl-6-nitroheptanoate hydrochloride (S)-2-Amino-6-methyl-6-nitroheptanoic acid (20.5 g) was dissolved in methanol (177 ml) and thionyl chloride (7.34 ml) was gently added dropwise under ice-cooling. The mixture was refluxed under heating for 2.5 h, and methanol was concentrated under reduced pressure to give the objective compound (21.9 g).

$^1$H-NMR(CDCl$_3$) δ ppm: 1.35–1.50(m,2H), 1.60(s,6H), 1.92–2.08(m,4H), 3.82(s,3H), 4.18(m,1H)

EXAMPLE 6 methyl (S)-2-t-butoxycarbonylamino-6-methyl-6-nitroheptanoate

Methyl (S)-2-amino-6-methyl-6-nitroheptanoate hydrochloride (21.9 g) was dissolved in methanol (88.5 ml) and water (40 ml) and the mixture was adjusted to pH 7.5 with saturated aqueous sodium hydrogencarbonate solution. di-tert-Butyl-dicarbonate (21.9 g, 100.4 mmol) was dissolved in methanol (44 ml) and added, and the mixture was stirred at room temperature for 1 h and at 40° C. for 2 h. Methanol was evaporated by concentration under reduced pressure and the residue was extracted with ethyl acetate (400 ml). The extract was washed with 0.5 mol/l hydrochloric acid (100 ml), saturated aqueous sodium hydrogencarbonate solution (100 ml) and saturated brine (100 ml) and dried over anhydrous magnesium sulfate. The anhydrous magnesium sulfate was removed by filtration and the residue was concentrated under reduced pressure to give the objective compound (25.7 g, yield 80.5%).

$^1$H-NMR(CDCl$_3$) δ ppm: 1.23–1.37(m,2H), 1.43(s,9H), 1.58–1.68(s+m,8H), 1.92(t,2H), 3.75(s,3H), 4.30(br,1H), 5.02(br,1H) mass spectrum m/e: 319(MH$^+$)

EXAMPLE 7

(S)-2-t-butoxycarbonylamino-6-methyl-6-nitroheptanoic acid (S)-2-Amino-6-methyl-6-nitroheptanoic acid (10.25 g, 50.2 mmol) was dissolved in methanol (40 ml) and water (25 ml). di-tert-Butyl-dicarbonate (10.92 g, 50.2 mmol) was dissolved in methanol (20 ml) and added, and the mixture was stirred at 40° C. for 1 h. di-tert-Butyl-dicarbonate (5.46 g, 25.1 mmol) was dissolved in methanol (10 ml) and added, and the mixture was stirred at 40° C. for 2.5 h. Methanol was evaporated by concentration under reduced pressure and ethyl acetate (200 ml) and 6N hydrochloric acid were added for pH adjustment to 2.0 and extraction. The mixture was washed with water (100 ml) and saturated brine (100 ml) and dried over anhydrous magnesium sulfate. The solvent was evaporated by concentration under reduced pressure to give the objective compound (7.66 g).

$^1$H-NMR(CDCl$_3$) δ ppm: 1.30–1.42(m,2H), 1.47(s,6H), 1.55(s,9H), 1.63–1.78(m,2H), 1.88–1.98(m,2H), 4.33(br, 1H), 5.00(br,11H)

EXAMPLE 8 methyl (S)-2-t-butoxycarbonylamino-6-methyl-6-nitroheptanoate (S)-2-t-Butoxycarbonylamino-6-methyl-6-nitroheptanoic acid (3.90 g, 12.81 mmol) was dissolved in dichloromethane (20 ml) and dimethylformamide dimethylacetal (2.6 ml, 19.22 mmol) was added. The mixture was stirred at room temperature for 20 h. Dimethylformamide dimethylacetal (1.74 ml, 12.8 mmol) was added and the mixture was stirred for 4 h. The mixture was washed with 0.5N hydrochloric acid (30 ml), saturated aqueous sodium hydrogencarbonate solution (30 ml) and saturated brine (30 ml). The solvent was evaporated by concentration under reduced pressure to give the objective compound (2.53 g, yield 62%).

EXAMPLE 9

Nα-t-butoxycarbonyl-6,6-dimethyl-L-lysine methyl ester

Methyl (S)-2-t-butoxycarbonylamino-6-methyl-6-nitroheptanoate (10.05 g, 31.6 mmol) was dissolved in methanol (200 ml). Iron powder (8.81 g, 157.8 mmol) and ferrous sulfate 7 hydrate (40.5 g, 145.6 mmol) were added and the mixture was stirred at 40° C. for 17 h. Since the starting material remained, the insoluble matter was removed by filtration. Iron powder (8.81 g, 157.8 mmol) and ferrous sulfate 7 hydrate (40.5 g, 145.6 mmol) were added and the mixture was stirred at 40° C. for 7 h. The insoluble material was removed by filtration, and methanol was removed by concentration under reduced pressure. Ethyl acetate (300 ml), water (100 ml) and 10% aqueous sodium carbonate solution were added for pH adjustment to 9 and extraction. Ethyl acetate was evaporated by concentration under reduced pressure to give the objective compound (5.01 g, yield 55.0%).

$^1$H-NMR(CDCl$_3$) δ ppm: 1.10(s,6H), 1.46(s,9H), 1.56–1.68(m,2H), 1.72(m,2H), 3.75(s,3H), 4.30(br,1H), 5.05(br,1H) $^{13}$C-NMR(CDCl$_3$) δ ppm: 19.30, 27.31, 28.74, 32.29, 42.82, 48.82, 51.24, 52.29, 78.89, 154.45, 172.44 mass spectrum m/e: 289(MH$^+$)

EXAMPLE 10

Nα-t-butoxycarbonyl-6,6-dimethyl-L-lysine methyl ester

Methyl (S)-2-t-butoxycarbonylamino-6-methyl-6-nitroheptanoate (500 mg, 1.57 mmol) was dissolved in methanol (8 ml) and water (0.5 ml), and 5% palladium-carbon (219 mg, 50% wet) and ferrous sulfate 7 hydrate (1.32 g, 4.75 mmol) were added. The mixture was stirred at a hydrogen pressure of 3 atm and room temperature for 3 h. Palladium-carbon was removed by filtration and methanol was evaporated by concentration under reduced pressure. Ethyl acetate (50 ml), water (50 ml) and sodium carbonate were added for pH adjustment to 10 and extraction. After layer partitioning, the aqueous layer was extracted again with toluene-isopropyl alcohol (1:1, 100 ml). The organic layers were combined and the solvent was evaporated by concentration under reduced pressure to give the objective compound (350 mg, yield 77.3%).

EXAMPLE 11

Nα-t-butoxycarbonyl-6,6-dimethyl-L-lysine methyl ester

Methyl (S)-2-t-butoxycarbonylamino-6-methyl-6-nitroheptanoate (300 mg, 0.94 mmol) was dissolved in methanol (10 ml) and 5% palladium-carbon (0.15 g, 50% wet) was added. The mixture was stirred at a hydrogen pressure of 20 atm and 80° C. for 24 h. Palladium-carbon was removed by filtration and methanol was evaporated by concentration under reduced pressure to give the objective compound (219 mg, yield 80.8%).

EXAMPLE 12

Nα-t-butoxycarbonyl-NE-t-butoxycarbonylmethyl-6,6-dimethyl-L-lysine methyl ester methanesulfonate Nα-t-Butoxycarbonyl-6,6-dimethyl-L-lysine methyl ester (1.0 g, 3.46 mmol) was dissolved in acetonitrile (30 ml), and diisopropylethylamine (1.60 ml, 9.19 mmol) and bromoacetyl t-butyl ester (0.812 g, 4.15 mmol) were added. The mixture was stirred at room temperature for about 20 h. Acetonitrile was evaporated by concentration under reduced pressure and ethyl acetate (30 ml) was added. The insoluble material was removed by filtration, and the mixture was washed twice with water (15 ml) and once with 10% sodium carbonate (15 ml) and dried over anhydrous sodium sulfate. Sodium sulfate was removed by filtration and methanesulfonic acid (0.2 ml) was added. The mixture was stirred at room temperature. The precipitated crystals were separated and dried under reduced pressure to give the objective compound (1.18 g, yield 68.5%).

$^1$H-NMR(DMSO-d$_6$) δ ppm: 1.22(s,6H), 1.25–1.43(m+s, 11H), 1.49–1.68(s+m,13H), 2.30(s,3H), 3.63(s,3H), 3.87(m, 2H), 3.98(m,1H) $^{13}$C-NMR(DMSO-d$_6$) δ ppm: 19.63, 22.37, 27.63, 28.14, 30.80, 36.60, 41.90, 51.70, 53.16, 59.12, 78.23, 83.09, 155.58, 166.41, 173.06 mass spectrum m/e: 403(MH$^+$)

REFERENCE EXAMPLE 4

4-methyl-4-nitrovaleronitrile

Acrylonitrile (6.0 g, 113 mmol), 2-nitropropane (12.0 g, 135 mmol) and hexadecyltrimethyl ammonium chloride (2.0 g) were stirred in a 0.1N aqueous sodium hydroxide solution (200 ml) overnight at room temperature. The layers were separated and the aqueous layer was extracted twice with methylene chloride (50 ml). The combined organic layer was washed with saturated brine (30 ml). The solvent was evaporated and the residue was dried to give oily 4-methyl-4-nitrovaleronitrile (10.4 g, 73 mmol, yield 64.6%).

$^1$H-NMR(CDCl$_3$) δ ppm: 1.65(s,6H), 2.28–4.46(m,4H)

REFERENCE EXAMPLE 5

4-methyl-4-nitropentanal

4-Methyl-4-nitrovaleronitrile (10.4 g, 13 mmol) was dissolved in methylene chloride (100 ml) and 1M diisobutyl aluminum hydride-hexane solution (100 ml) was added dropwise at −50° C. The mixture was stirred for 0.5 h, and water (8 ml) was added gradually, after which magnesium sulfate (5.0 g) was added. The mixture was filtrated and 1N hydrochloric acid (50 ml) was added. The mixture was stirred for 0.5 h and the layers were separated. The organic layer was washed with saturated brine and the solvent was evaporated. The residue was dried to give oily 4-methyl-4-nitropentanal (6.9 g, 48 mmol).

$^1$H-NMR(CDCl$_3$) δ ppm: 1.60(s,6H), 2.25(t,2H), 2.52(t, 2H), 9.79(s,1H)

EXAMPLE 13

5-(4-methyl-4-nitropentylidene)hydantoin

Oily 4-methyl-4-nitropentanal (4.0 g, 28 mmol), hydantoin (4.0 g, 40 mmol) and sodium carbonate (2.8 g, 20 mmol) were added to 50% aqueous acetonitrile (200 ml) and the mixture was refluxed with stirring for 3 days. The reaction mixture was concentrated and extracted three times with ethyl acetate. The organic layer was concentrated to dryness to give 5-(4-methyl-4-nitropentylidene)hydantoin (3.15 g, 13.9 mmol, yield 50.0%).

$^1$H-NMR(DMSO-d$_6$) δ ppm: 1.56(s,6H), 2.00(m,2H), 2.13(m,2H), 5.42(t,1H) mass spectrum m/e: 226(MH$^-$)

EXAMPLE 14

5-(4-methyl-4-nitropentylidene)hydantoin

Water (70 ml) was added to hydantoin (20.8 g, 210 mmol) and sodium carbonate (7.2 g, 70 mmol) and the mixture was dissolved by heating to 85° C. 4-Methyl-4-nitropentanal (20.0 g, 140 mmol) was dissolved in isopropyl alcohol (130 ml) and added. The mixture was refluxed under heating for 2 h and isopropyl alcohol was evaporated under reduced pressure. Water (20 ml) and concentrated hydrochloric acid were added to adjust its pH to 8. The precipitated crystals were separated and dried to give 5-(1-hydroxy-4-methyl-4-nitropentylidene)hydantoin (27.3 g). This compound (19.4 g, 78.9 mmol) was dissolved in pyridine (60 ml) and methanesulfonyl chloride (7.9 ml, 102.6 mmol) was added under ice-cooling. The mixture was stirred at room temperature for 3 h. Water (50 ml) was added and the mixture was extracted three times with ethyl acetate (50 ml). The extract solutions were combined and washed 4 times with 1 mol hydrochloric acid (50 ml). After separation of layers, the organic layer was concentrated to dryness to give 5-(1-methanesulfonyloxy-4-methyl-4-nitropentylidene)hydantoin (20.5 g). To this compound (5.74 g, 17.8 mmol) were added tetrahydrofuran (80 ml) and 1,8-diazabicyclo[5.4.0]undec-7-ene (2.7 ml, 17.8 mmol) and the mixture was stirred at room temperature for 4 h. Tetrahydrofuran was concentrated under reduced pressure and the residue was extracted with ethyl acetate (50 ml) and 0.5 M hydrochloric acid (80 ml). After separation of layers, ethyl acetate was concentrated to dryness to give 5-(4-methyl-4-nitropentylidene) hydantoin (4.0 g, 17.6 mmol, yield 61.6%).

EXAMPLE 15

5-(4-methyl-4-nitropentyl)hydantoin

To 5-(4-methyl-4-nitropentylidene)hydantoin (3.15 g, 13.9 mmol) were added methanol (60 ml) and water (10 ml), and the mixture was reduced by the addition of palladium-carbon (2.2 g) and hydrogen. After the reaction, palladium-carbon was filtered off and the residue was concentrated to dryness. Decantation with water and dichloromethane gave 5-(4-methyl-4-nitropentyl)hydantoin (1.1 g).

$^1$H-NMR(DMSO-d$_6$) δ ppm: 1.18–1.30(m,2H), 1.52(s, 6H), 2.55–2.70(m,2H), 2.83–2.90(m,2H), 3.96–4.01(m,1H) mass spectrum m/e: 228(MH$^-$)

EXAMPLE 16

5-(4-methyl-4-nitropentyl)hydantoin

Methanol (200 ml) was added to 5-(4-methyl-4-nitropentylidene)hydantoin (25.85 g, 114 mmol) and 27% aqueous sodium hydroxide solution was added to adjust the pH to 10 for dissolution. Palladium-carbon (1.1 g) and hydrogen were added for reduction. After the reaction, palladium-carbon was filtered off and methanol was evaporated by concentration under reduced pressure. Water (50 ml) was added and the pH was adjusted to 2 with concentrated hydrochloric acid. The precipitated crystals were separated and dried to give 5-(4-methyl-4-nitropentyl)hydantoin (19.02 g, 83 mmol, yield 72.9%).

In the following Examples, 2-amino-6-methyl-6-nitroheptanoic acid was quantitatively determined by high performance liquid chromatography (HPLC) using a column "Inertsil ODS-2" (φ4.6×250 mm) manufactured by GL Sciences Inc. The analysis conditions were as follows.

mobile phase: 30 mM aqueous phosphoric acid solution/methanol=8/2(V/V)
flow rate: 1.0 ml/min.
column temperature: 50° C.
detection: UV 210 nm The optical purity of 2-amino-6-methyl-6-nitroheptanoic acid was measured by high performance liquid chromatography using an optical resolution column "CROWNPAK CR(+)" (φ4.6×250 mm) manufactured by DAICEL CHEMICAL INDUSTRIES, LTD. The analysis conditions were as follows.

mobile phase: aqueous perchloric acid solution (pH 1.8)/acetonitrile=8/2(V/V)
flow rate: 1.0 ml/min.
column temperature: 50° C.
detection: UV 210 nm Under these conditions, fractional quantitation was performed at 4.4 min retention time for (R)-2-amino-6-methyl-6-nitroheptanoic acid and at 6.1 min retention time for (S)-2-amino-6-methyl-6-nitroheptanoic acid.

EXAMPLE 17

A medium (pH 7.0) containing glucose 0.5%, ammonium sulfate 0.5%, yeast extract powder 1.0%, peptone 1.0%, KH$_2$PO$_4$ 0.1%, K$_2$HPO$_4$ 0.3%, MgSO$_4$.7H$_2$O 0.05%, FeSO$_4$.7H$_2$O 0.001%, MnSO$_4$.5H$_2$O 0.001% and DL-5-indolylmethylhydantoin 0.25% was dispensed by 50 ml to a 500 ml Sakaguchi flask, and sterilized at 120° C. for 10 min. After cooling, *Microbacterium liquefaciens* AJ3940 cultured on an agar plate containing glucose 0.5%, ammonium sulfate 0.5%, yeast extract powder 1.0% and peptone 1.0% at 30° C. for 24 h was inoculated by one platinum loop and subjected to aerobic shake culture at 30° C. for 20 h. Thereafter, it was centrifuged (12,000 g, 10 min) and bacterial cells were collected, which were suspended in 100 mM Tris-hydrochloric acid buffer (pH 8.0, 40 ml). The suspension was centrifuged again in the same manner to give washed bacterial cells. To the washed bacterial cells was added the same weight of the same Tris-hydrochloric acid buffer to prepare a bacterial cell suspension. DL-5-(4-Methyl-4-nitropentyl)hydantoin was weighed by 100 mg and suspended in 16 ml of 100 mM Tris-hydrochloric acid buffer (pH 8.0) and used as a substrate solution. To the substrate solution was added 4 ml of the bacterial cell suspension and the mixture was incubated at 37° C. The amount of 2-amino-6-methyl-6-nitroheptanoic acid generated in the reaction mixture at 6, 20, 30, 44, 68 and 96 hours after the start of the reaction is shown in Table 1.

TABLE 1

| Reaction time (min) | 2-amino-6-methyl-6-nitrohepanoic acid (g/dl) generated | Residual substrate (g/dl) |
| --- | --- | --- |
| 0 | 0 | 0.50 |
| 6 | 0.02 | 0.45 |
| 20 | 0.04 | 0.38 |
| 30 | 0.09 | 0.27 |
| 44 | 0.15 | 0.20 |
| 68 | 0.20 | 0.17 |
| 96 | 0.33 | 0.07 |

EXAMPLE 18

In the same manner as in Example 17, the reaction mixture (70 ml) was prepared and reacted for 120 h. After the reaction, the reaction mixture (containing 207 mg of 2-amino-6-methyl-6-nitroheptanoic acid) was diluted in water (200 ml) and centrifuged (12,000 g, 10 min) to remove the bacterial cells. Then, the supernatant was passed through a cation exchange resin column (AMBERLITE IR-120B, column diameter 2.6 cm×length 20 cm) (flow rate 3 ml/min) to allow adsorption of 2-amino-6-methyl-6-nitroheptanoic acid. The column was washed with 500 ml of water and then 2% aqueous ammonia (300 ml) was passed through the column (flow rate 3 ml/min) to elute 2-amino-6-methyl-6-nitroheptanoic acid. The eluate was concentrated under reduced pressure to 3 ml using a rotary evaporator at 40° C. Acetone was dropwise added thereto to give 2-amino-6-methyl-6-nitroheptanoic acid as an ammonium salt (dry weight 130 mg). The obtained 2-amino-6-methyl-6-nitroheptanoic acid was subjected to HPLC analysis using an optical resolution column, CROWNPAK CR(+). As a result, the obtained acid was found to be an L-enantiomer (S-enantiomer) having an optical purity of not less than 99% e.e.

EXAMPLE 19

*Agrobacterium* sp. AJ11220 strain cultured on an agar plate containing glucose 0.5%, ammonium sulfate 0.5%, yeast extract powder 1.0% and peptone 1.0% at 30° C. for 24 h was plated on the entirety of an agar plate (pH 7.0) containing glucose 0.5%, ammonium sulfate 0.5%, yeast extract powder 1.0%, peptone 1.0%, KH$_2$PO$_4$ 0.1%, K$_2$HPO$_4$ 0.3%, MgSO$_4$.7H$_2$O 0.05%, FeSO$_4$.7H$_2$O 0.001%, MnSO$_4$.5H$_2$O 0.001% and DL-5-indolylmethylhydantoin 0.25% and aerobically cultured at 30° C. for 24 h. The bacterial cell was scraped and suspended in the same weight of 100 mM Tris-hydrochloric acid buffer (pH 8.0) to give a bacterial cell suspension. Then, DL-5-(4-methyl-4-nitropentyl)hydantoin (100 mg) and sodium sulfite (50 mg) were weighed and added to 8 ml of 100 mM Tris-hydrochloric acid buffer (pH 8.0), which was used as a substrate solution. To the substrate solution was added 2 ml of the bacterial cell suspension and the mixture was incubated at 30° C. The amount of 2-amino-6-methyl-6-nitroheptanoic acid generated in the reaction mixture at 1.5, 3, 6 and 20 hours after the start of the reaction is shown in Table 2. The reaction mixture after 20 hours from the start of the reaction was diluted with water and bacterial cells were removed. The resulting liquid was subjected to HPLC analysis using an optical resolution column, CROWNPAK CR(+). As a result, the obtained acid was found to be a D-enantiomer (R-enantiomer) having an optical purity of not less than 94% e.e.

TABLE 2

| Reaction time (min) | 2-amino-6-methyl-6-nitroheptanoic acid (g/dl) generated |
|---|---|
| 0 | 0 |
| 1.5 | 0.12 |
| 3 | 0.18 |
| 6 | 0.28 |
| 20 | 0.42 |

EXAMPLE 20

A medium (pH 7.0) containing maltose 2%, ammonium sulfate 0.5%, yeast extract powder 1.0%, peptone 1.0%, $KH_2PO_4$ 0.1%, $K_2HPO_4$ 0.3%, $MgSO_4.7H_2O$ 0.05%, $FeSO_4.7H_2O$ 0.001%, $MnSO_4.5H_2O$ 0.001% and DL-5-isopropylhydantoin 0.2% was dispensed by 50 ml to a 500 ml Sakaguchi flask, and sterilized at 120° C. for 10 min. After cooling, Bacillus sp. AJ12299 cultured on an agar plate containing glucose 0.5%, ammonium sulfate 0.5%, yeast extract powder 1.0% and peptone 1.0% at 30° C. for 24 h was inoculated by one platinum loop and subjected to aerobic shake culture at 30° C. for 20 h. Thereafter, it was centrifuged (12,000 g, 10 min) and bacterial cells were collected, which were suspended in 100 mM potassium phosphate buffer (pH 7.0, 40 ml). The suspension was centrifuged again in the same manner to give washed bacterial cell. To the washed bacterial cell was added the same weight of the same potassium phosphate buffer to prepare a bacterial cell suspension. DL-5-(4-Methyl-4-nitropentyl)hydantoin (1.25 g/dl), glucose (1.25 g/dl) and $MgSO_4.7H_2O$ (0.05 g/dl) were added to 100 mM potassium phosphate buffer (pH 7.0) and used as a substrate solution. To the substrate solution (4 ml) was added 1 ml of the bacterial cell suspension and the mixture was aerobically incubated while shaking in a test tube at 30° C. for 48 h. After the reaction, concentrated hydrochloric acid (0.4 ml) and 300 mM $NaNO_2$ (0.2 ml) were added to the reaction mixture (2.0 ml) under ice-cooling and the mixture was stood at 4° C. for 24 h, whereby N-carbamyl-2-amino-6-methyl-6-nitroheptanoic acid generated by the reaction using the bacterial cell was decarbamylated. The concentration of 2-amino-6-methyl-6-nitroheptanoic acid generated in the reaction mixture after decarbamylation was measured to be 0.51 g/dl. In addition, optical activity was measured. As a result, it was found that the compound was an L-enantiomer (S-isomer) having an optical purity of not less than 99% e.e.

REFERENCE EXAMPLE 6

It was clarified by re-identification that Flavobacterium sp. AJ3912 strain and AJ3940 strain were Microbacterium liquefaciens (former Aureobacterium liquefaciens).

That is, a physiological test was conducted and analyzed against Bergey's Manual of Determinative Bacteriology, vol. 1 (9th Ed., 1994, Williams & Wilkins), which is a taxonomy book of bacteria. The following physiological properties were found.

| test | |
|---|---|
| Gram stain | positive |
| mobility | absent |
| nitrate reduction | − |
| pyrimidinase | − |
| pyridonylallyl amidase | − |
| alkaline phosphatase | + |
| β-glucuronidase | − |
| β-galactosidase | + |
| α-glucosidase | + |
| N-acetyl-β-glucosaminidase | + |
| esculin (glucosidase) | + |
| urease | − |
| gelatin liquefaction | + |
| fermentability of carbohydrate | |
| glucose | − |
| ribose | − |
| xylose | − |
| mannitol | − |
| maltose | − |
| lactose | − |
| sucrose | − |
| glycogen | − |
| anaerobic growth | − |
| casein hydrolysis | + |

REFERENCE EXAMPLE 7

It was clarified by re-identification that the Pseudomonus hydantoinophilum AJ11220 strain was Agrobacterium sp.

That is, a physiological test was conducted and analyzed against Bergey's Manual of Determinative Bacteriology, vol. 1 (9th Ed., 1994, Williams & Wilkins), which is a taxonomy book of bacteria. The following physiological properties were found.

| test | |
|---|---|
| cell size and shape | 0.8 × 1.5–2.0 μm |
| Gram stain | − |
| spore | − |
| motility and flagellar arrangement | +: peritrichous |
| catalase | + |
| oxidase | + |

| test | |
|---|---|
| O-F test | − |
| nitrate reduction | + |
| indole formation | − |
| acid production from D-glucose | − |
| arginine dihydrolase reaction | − |
| urease | + |
| esculin hydrolysis | + |
| gelatin hydrolysis | − |
| β-galactosidase | + |
| utilization of carbon compounds | |
| glucose | + |
| L-arabinose | + |
| D-mannose | + |
| D-mannitol | + |
| N-acetyl-D-glucosamine | + |
| maltose | + |
| potassium gluconate | − |
| n-caprate | − |
| adipate | − |
| dl-malic acid | + |
| sodium citrate | − |
| phenylacetate | − |

According to the present invention, optically active lysine derivatives of the aforementioned formulas (3) and (5) useful as pharmaceutical intermediates can be produced by an industrial method.

This application is based on patent application Nos. 213181/2000, 334579/2000 and 118508/2001 filed in Japan, the contents of which are hereby incorporated by reference.

What is claimed is:

1. A compound of formula (18), a salt thereof, an optically active substance thereof or a racemate thereof:

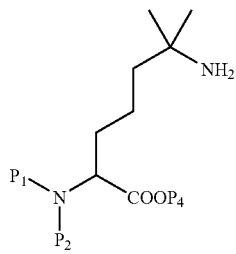

(18)

wherein $P_1$ and $P_2$ are each independently an amino-protecting group or hydrogen atom where $P_1$ and $P_2$ are not hydrogen atoms at the same time, or $P_1$ and $P_2$ in combination show an amino-protecting group except phthaloyl group, and $P_4$ is a hydrogen atom or a carboxyl-protecting group.

2. A compound of formula (23):

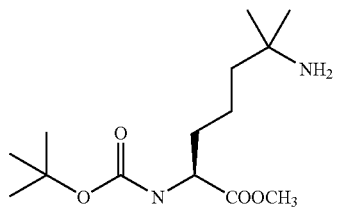

(23)

or a salt thereof.

* * * * *

UNITED STATES PATENT AND TRADEMARK OFFICE
CERTIFICATE OF CORRECTION

PATENT NO.       : 7,148,371 B2                                             Page 1 of 1
APPLICATION NO.  : 11/211442
DATED            : December 12, 2007
INVENTOR(S)      : Masakazu Nakazawa et al.

It is certified that error appears in the above-identified patent and that said Letters Patent is hereby corrected as shown below:

On the title page, item (75) should read:

--(75) Inventors:  Masakazu NAKAZAWA
                   Daisuke TAKAHASHI
                   Kunisuke IZAWA--

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,148,371 B2  Page 1 of 1
APPLICATION NO. : 11/211442
DATED : December 12, 2006
INVENTOR(S) : Masakazu Nakazawa et al.

It is certified that error appears in the above-identified patent and that said Letters Patent is hereby corrected as shown below:

On the title page, item (75) should read:

--(75) Inventors: Masakazu NAKAZAWA
Daisuke TAKAHASHI
Kunisuke IZAWA--

This certificate supersedes the Certificate of Correction issued December 11, 2007.

Signed and Sealed this

First Day of January, 2008

JON W. DUDAS
*Director of the United States Patent and Trademark Office*